United States Patent
Pouliot et al.

(10) Patent No.: US 7,087,736 B1
(45) Date of Patent: Aug. 8, 2006

(54) TYROSINE DNA PHOSPHODIESTERASES (TDP) AND RELATED POLYPEPTIDES NUCLEIC ACIDS VECTORS TDP PRODUCING HOST CELLS ANTIBODIES AND METHODS OF USE

(75) Inventors: Jeffrey Pouliot, San Mateo, CA (US); Howard A. Nash, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 422 days.

(21) Appl. No.: 10/110,176

(22) PCT Filed: Oct. 5, 2000

(86) PCT No.: PCT/US00/27400

§ 371 (c)(1),
(2), (4) Date: Jun. 27, 2002

(87) PCT Pub. No.: WO01/25407

PCT Pub. Date: Apr. 12, 2001

Related U.S. Application Data

(60) Provisional application No. 60/157,690, filed on Oct. 5, 1999.

(51) Int. Cl.
*C07H 21/04* (2006.01)
*C12N 1/21* (2006.01)
*C12N 5/10* (2006.01)
*C12N 15/55* (2006.01)
*C12N 15/63* (2006.01)
C12N 9/16

(52) U.S. Cl. ............... 536/23.2; 435/196; 435/198; 435/252.3; 435/320.1; 435/325

(58) Field of Classification Search ............... 536/23.2, 536/23.5, 24.31; 435/196, 198, 252.3, 320.1, 435/325, 199, 254.11
See application file for complete search history.

(56) References Cited

U.S. PATENT DOCUMENTS

2003/0073623 A1 * 4/2003 Drmanac et al. ............. 514/12

2003/0096951 A1 * 5/2003 Jacobs et al. ............... 530/350

FOREIGN PATENT DOCUMENTS

WO WO 92 18541 A 10/1992
WO WO 97 15676 A 5/1997

OTHER PUBLICATIONS

Hillier et al (Mar. 9, 1998) GenBank accession AA620407.*
Aboussekhra et al., *EMBO Journal*, 15(15):3912–3922 (1996).
DuBois E., *Database EMBL Online!*, EMBL:SCYBR223C, "*S. cerevisiae* chromosome II reading frame ORF YBR223c," XP002161092 Abstract (Sep. 6, 1994).
Feldmann, et al., *EMBO Journal*, 13(24):5795–5809 (Dec. 15, 1994).
Knab, et al., *Journal of Biological Chemistry*, 268(30):22322–22330 (Oct. 25, 1993).
Megonigal, et al., *Journal of Biological Chemistry*, 272(19):12801–12808 (May 9, 1997).
Pouliot et al., *Science* 286(5439):552–555 (Oct. 15, 1999).
Strausberb R., *Database EMBL Online!*, EMBL:AW007897, XP002161091 Abstract (Sep. 13, 1999).
Wang, James C., *Annu. Rev. Biochem.*, 65:635–692 (1996).
Wilson et al., *Nature*, 368:32–38 (Mar. 3, 1994).
Wilson R., *Database Swall Online!*, SWALL:Q19973, "Caenorhabditis elegans," XP002161093 (Nov. 1, 1996).
Yang et al., *Proc. Natl. Acad. of Sci. USA*, 93(21):11534–11539 (Oct. 1996).

* cited by examiner

*Primary Examiner*—Elizabeth Slobodyansky
(74) *Attorney, Agent, or Firm*—Leydig, Voit & Mayer, Ltd.

(57) ABSTRACT

The present invention provides a nucleic acid molecule encoding a tyrosine-DNA phosphodiesterase (TDP), and a related vector, host cell, polypeptide, antibody, antisense nucleic acid molecule, and ribozyme. Also provided are a method of altering the level of TDP in a cell, tissue, organ or organism, as well as the resulting cell, tissue, organ or non-human organism, as well as a method of identifying a TDP-resistant compound, a method of assessing TDP1 activity in an animal, and a method of assessing the efficacy of a topoisomerase I inhibitor.

14 Claims, 7 Drawing Sheets

```
   1  CCGAGGCAAG CGTTGGTTCT GTGCGCCTCA GGAGTATAAT GTCTCAGGAA
  51  GGCGATTATG GGAGGTGGAC CATATCTAGT AGTGATGAAA GTGAGGAAGA
 101  AAAGCCAAAA CCAGACAAGC CATCTACCTC TTCTCTTCTC TGTGCCAGGC
 151  AAGGAGCAGC AAATGAGCCC AGGTACACCT GTTCCGAGGC CCAGAAAGCT
 201  GCACACAAGA GGAAAATATC ACCTGTGAAA TTCAGCAATA CAGATTCAGT
 251  TTTACCTCCC AAAAGGCAGA AAAGCGGTTC CCAGGAGGAC CTCGGCTGGT
 301  GTCTGTCCAG CAGTGATGAT GAGCTGCAAC CAGAAATGCC GCAGAAGCAG
 351  GCTGAGAAAG TGGTGATCAA AAAGGAGAAA GACATCTCTG CTCCCAATGA
 401  CGGCACTGCC CAAAGAACTG AAAATCATGG CGCTCCCGCC TGCCACAGGC
 451  TCAAAGAGGA GGAAGACGAG TATGAGACAT CAGGGGAGGG CCAGGACATT
 501  TGGACATGC TGGATAAAGG GAACCCCTTC CAGTTTTACC TCACTAGAGT
 551  CTCTGGAGTT AAGCCAAAGT ATAACTCTGG AGCCCTCCAC ATCAAGGATA
 601  TTTTATCTCC TTTATTTGGG ACGCTTGTTT CTTCAGCTCA GTTAACTAC
 651  TGCTTTGACG TGGACTGGCT CGTAAAACAG TATCCACCAG AGTTCAGGAA
 701  GAAGCCAATC CTGCTTGTGC ATGGTGATAA GCGAGAGGCT AAGGCTCACC
 751  TCCATGCCCA GGCCAAGCCT TACGAGAACA TCTCTCTCTG CCAGGCAAAG
 801  TTGGATATTG CGTTtggaac acaCCACACG AAAATGATGC TGCTGCTCTA
 851  TGAAGAAGGC CTCCGGGTTG TCATACACAC CTCCAACCTC ATCCATGCTG
 901  ACTGGCACCA GAAAACTCAA GGAATATGGT TGAGCCCCTT ATACCCACGA
 951  ATTGCTGATG GAACCCACAA ATCTGGAGAG TCGCCAACAC ATTTTAAAGC
1001  TGATCTCATC AGTTACTTGA TGGCTTATAA TGCCCCTTCT CTCAAGGAGT
1051  GGATAGATGT CATTCACAAG CACGATCTCT CTGAAACAAA TGTTTATCTT
1101  ATTGGTTCAA CCCCAGGACG CTTTCAAGGA AGTCAAAAAG ATAATTGGGG
1151  ACATTTTAGA CTTAAGAAGC TTCTGAAAGA CCATGCCTCA TCCATGCCTA
1201  ACGCAGAGTC CTGGCCTGTC GTAGGTCAGT TTTCAAGCGT TGGCTCCTTG
```

Fig. 1

```
1251  GGAGCCGATG AATCAAAGTG GTTATGTTCT GAGTTTAAAG AGAGCATGCT
1301  GACACTGGGG AAGGAAAGCA AGACTCCAGG AAAAAGCTCT GTTCCTCTTT
1351  ACTTGATCTA TCCTTCTGTG GAAAATGTGC GGACCAGTTT AGAAGGATAT
1401  CCTGCTGGGG GCTCTCTTCC CTATAGCATC CAGACAGCTG AAAAACAGAA
1451  TTGGCTGCAT TCCTATTTTC ACAAATGGTC AGCTGAGACT TCTGGCCGCA
1501  GCAATGCCAT GCCACATATT AAGACATATA TGAGGCCTTC TCCAGACTTC
1551  AGTAAAATTG CTTGGTTCCG TGTCACAAGC GCAAATCTGT CCAAGGCTGC
1601  CTGGGGAGCA TTGAGAAGA ATGGCACCCA GCTGATGATC CGCTCCTACG
1651  AGCTCGGGGT CCTTTTCCTC CCTTCAGCAT TTGGTCTAGA CAGTTTCAAA
1701  GTGAAACAGA AGTTCTTCGC TGGCAGCCAG GAGCCAATGG CCACCTTTCC
1751  TGTGCCATAT GATTTGCCTC CAGAACTGTA TGGAAGTAAA GATCGGCCAT
1801  GGATATGGAA CATTCCTTAT GTCAAAGCAC CGGATACGCA TGGGAACATG
1851  TGGGTGCCCT CCTGAGAATC TTGAGGCACT GTGAAATTTA AGTGTAAGAC
1901  ATTGAGCCAC AAACATGGAA TCTCTTCTTT GTACTGGATG TCCACTTCCC
1951  TTAAAGTCTT ATTTGCACCC TTACAAAATC TTTCCAAAGG TCACTCTTAT
2001  GAATGGATGT TGGTTATACT TTTAATGGAC ATTAACATTC CTAATAAAGT
2051  ATTAGTTTCT TAAAAAAAAA AAAAAAAAA AAAAAAAAA A
```

Fig.1 (Cont.)

```
  1   EASVGSVRLR  SIMSQEGDYG  RWTISSSDES  EEEKPKPDKP  STSSLLCARQ
 51   GAANEPRYTC  SEAQKAAHKR  KISPVKFSNT  DSVLPPKRQK  SGSQEDLGWC
101   LSSSDDELQP  EMPQKQAEKV  VIKKEKDISA  PNDGTAQFTE  NHGAPACHRL
151   KEEEDEYETS  GEGQDIWDML  DKGNPFQFYL  TRVSGVKPKY  NSGALHIKDI
201   LSPLFGTLVS  SAQFNYCFDV  DWLVKQYPPE  FRKKPILLVH  GDKREAKAHL
251   HAQAKPYENI  SLCQAKLDIA  FGTHHTKMML  LLYEEGLRVV  IHTSNLIHAD
301   WHQKTQGIWL  SPLYPRIADG  THKSGESPTH  FKADLISYLM  AYNAPSLKEW
351   IDVIHKHDLS  ETNVYLIGST  PGRFQGSQKD  NWGHFRLKKL  LKDHASSMPN
401   AESWPVVGQF  SSVGSLGADE  SKWLCSEFKE  SMLTLGKESK  TPGKSSVPLY
451   LIYPSVENVR  TSLEGYPAGG  SLPYSIQTAE  KQNWLHSYFH  KWSAETSGRS
501   NAMPHIKTYM  RPSPDFSKIA  WFRVTSANLS  KAAWGALEKN  GTQLMIRSYE
551   LGVLFLPSAF  GLDSFKVKQK  FFAGSQEPMA  TFPVPYDLPP  ELYGSKDRPW
601   IWNIPYVKAP  DTHGNMWVPS  *ES*GTVKFK  CKTLSHKHGI  SSLYWMSTSL
651   KVLFAPLQNL  SKGHSYEWML  VILLMDINIP  NKVLVS*KKK  KKKKKK
```

Fig. 2

```
   1  ATGTCACGAG AAACAAATTT CAATGGAACT AAGAGGAAGA GGTCGGATGT
  51  TGCCGAGAAA GTAGCACAAC GGTGGAAGAG CGTCAGGTAT AGTGCTGAAA
 101  TGGAGAATAT GGCTCCGGTC AACAGTAACA ATGATAGCGA CGACTGCGTC
 151  ATAGTCAGTG AATCGAAAAT CATTGATTTG ACTAATCAGG AACAAGATTT
 201  GAGTGAGAGA ATAGAAACAA ACGATACGGC AAAAGGTGCC GTTTTAAAC
 251  TAATGAAATC GGACTTCTAT GAAAGAGAGG ATTTTATGGG AGAAGTAGAG
 301  GATATGATTA CATTGAAAGA TATCTTTGGC ACTGAGACAC TAAAAAGAAG
 351  CATACTCTTC AGTTTCCAAT ACGAACTTGA TTTCTTGTTG AGACAATTCC
 401  ACCAGAACGT AGAGAACATA ACCATCGTCG GCCAAAAGGG TACTATTATG
 451  CCTATCGAAG CCCGTGCTAT GGACGCGACA CTGGCAGTAA TATTAAAAAA
 501  GGTCAAACTT ATTGAAATAA CGATGCCCCC ATTCGCTTCC CACCATACGA
 551  AGCTGATCAT AAACTTTTAC GATAATGGCG AATGCAAAAT ATTCTTGCCA
 601  TCTAACAATT TTACGTCAAT GGAGACTAAC CTGCCTCAAC AGGTGTGTTG
 651  GTGCAGTCCC CTTTTGAAAA TAGGTAAAGA AGGGCTACCA GTACCGTTTA
 701  AGAGAAGCTT GATAGAATAC CTCAATTCGT ACCACCTGAA AGACATTGAC
 751  GAATTGATTA CAAAAAGCGT AGAGGAAGTT AACTTTGCTC CTTTGAGCGA
 801  ATTAGAATTT GTATATTCTA CGCCCTCCAA ATTTCAGTCG TCGGGTTTAC
 851  TGTCGTTTTA CAATAAACTA GAAAAACTTT CTGCTGGCAC AAGTGCTAGT
 901  GATACTGCAA ACATTATCT ATGTCAAACT TCATCCATAG GACATCTCT
 951  ATCAAGAGCG CGAGACGAAA ACTTATGGAC ACATCTAATG ATTCCTCTGT
1001  TTACCGGAAT CATGTCCCCT CCAGCAAAGG ACACCGCTGG GAGGAAGAAA
1051  GCAGAAATAC TGCCAACGAA TTCATTGATT AATGAATATT CGCAGAGAAA
1101  AATCAAGCCG TACATTATTT TCCCCACCGA ACAAGAGTTT GTCACCAGTC
1151  CCTTAAAGTG GTCCAGTTCC GGGTGGTTTC ATTTTCAATA TCTTCAGAAA
1201  AAGAGCTACT ACGAAATGCT GCGAAACAAG TTCAAAGTAT TTTACAAGCA
```

Fig. 3

```
1251  AGACCCTGCT ATGGTTACTA GAAGACGAGG GACGACGCCC GCGCACTCTA

1301  AGTTTTACAT GCATTGTGCA ACAAACTCCG CAGGGCCCTG TGATGCATCG

1351  CAGGTATTTA AAGAACTAGA ATGGTGCCTT TATACTTCGG CAAACCTCAG

1401  CCAAACAGCA TGGGGCACCG TTTCAAGAAA ACCACGCAAT TATGAAGCAG

1451  GAGTGCTTTA CCATAGTCGC AGGTTAGCAA ATACCAGGAA GGTCACGTGC

1501  CGTACTTTTA CACGTGACCG TAGAGGCTGC GCGGGTAATC CCACCCATGT

1551  GGCCGTGCCA TTCACGCTGC CAGTCATACC ATACGACTTA GCTGAGGACG

1601  AGTGCTTTTG CCTTGCTCGT CATGAGAACG ACTAA
```

Fig. 3 (Cont.)

```
  1  MSRETNFNGT KRKRSDVAEK VAQRWKSVRY SAEMENMAPV NSNNDSDDCV
 51  IVSESKIIDL TNQEQDLSER IETNDTAKGA VFKLMKSDFY EREDFMGEVE
101  DMITLKDIFG TETLKRSILF SFQYELDFLL RQFHQNVENI TIVGQKGTIM
151  PIEARAMDAT LAVILKKVKL IEITMPPFAS HHTKLIINFY DNGECKIFLP
201  SNNFTSMETN LPQQVCWCSP LLKIGKEGLP VPFKRSLIEY LNSYHLKDID
251  ELITKSVEEV NFAPLSELEF VYSTPSKFQS SGLLSFYNKL EKLSAGTSAS
301  DTAKHYLCQT SSIGTSLSRA RDENLWTHLM IPLFTGIMSP PAKDTAGRKK
351  AEILPTNSLI NEYSQRKIKP YIIFPTEQEF VTSPLKWSSS GWFHPQYLQK
401  KSYYEMLRNK FKVFYKQDPA MVTRRRGTTP AHSKFYMHCA TNSAGPCDAS
451  QVFKELEWCL YTSANLSQTA WGTVSRKPRN YEAGVLYHSR RLANTRKVTC
501  RTFTRDRRGC AGNPTHVAVP FTLPVIPYDL AEDECFCLAR HEND*
```

TYROSINE DNA PHOSPHODIESTERASES (TDP) AND RELATED POLYPEPTIDES NUCLEIC ACIDS VECTORS TDP PRODUCING HOST CELLS ANTIBODIES AND METHODS OF USE

CROSS-REFERENCE TO RELATED APPLICATIONS

This application is the U.S. national phase of PCT/US00/27400, which was filed on Oct. 5, 2000, and which claims priority to U.S. provisional application Ser. No. 60/157,690, which was filed on Oct. 5, 1999.

TECHNICAL FIELD OF THE INVENTION

The present invention relates to tyrosine-DNA phosphodiesterases and related polypeptides, nucleic acids, vectors, TDP-producing host cells, antibodies and methods of use in the identification of a TDP-resistant compound, in the assessment of TDP1 activity in an animal, and in the assessment of efficacy of a topoisomerase I inhibitor.

BACKGROUND OF THE INVENTION

Topoisomerases are cellular enzymes that are crucial for replication and transcription of the cellular genome. Topoisomerases cleave the DNA backbone, thereby allowing topological change for replication and transcription of the cellular genome to occur, after which topoisomerases reseal the DNA backbone (Wang, Ann. Rev. Biochem. 65: 635 (1996)). Topoisomerases are efficient because DNA breakage is accompanied by covalent bonding between the enzyme and the DNA to create an intermediate that is resolved during the resealing step. This mechanism, while elegant, makes topoisomerases potentially dangerous. If the resealing step fails, a normally transient break in DNA becomes a long-lived disruption, one with a topoisomerase covalently joined to it. Unless a way is found to restore the continuity of the DNA the cell will die.

In virtually all topoisomerases, the heart of the covalent complex is a phosphodiester bond between a specific tyrosine residue of the enzyme and one end of the break (the 3' end for eukaryotic topoisomerase I and the 5' end for topoisomerases II and III). The high-energy nature of this bond normally ensures the resealing step.

Failure of resealing is dramatically increased by several drugs, such as camptothecin, a promising anti-cancer agent that specifically targets eukaryotic topoisomerase I (Chen et al., Ann. Rev. Pharmacol. Toxicol. 34: 191 (1994)). Protein-linked breaks also accumulate when topoisomerases act on DNA containing structural lesions like thymine dimers, abasic sites and mismatched base pairs (Pommier et al., Biochim. Biophys. Acta 1400: 83 (1998)). To the extent that such lesions arise during the normal life of a cell, topoisomerase-associated damage may be unavoidable.

Repair of topoisomerase-DNA covalent complexes is of obvious value to the cell but, until the present invention, very little was known about the mechanisms involved in such repair. Hydrolysis of the bond joining the topoisomerase to DNA had been proposed as a way to effect release of the topoisomerase such that the cleaved DNA could undergo conventional modes of break repair (Friedberg et al., *DNA Repair and Mutagenesis* (ASM Press, Washington, D.C. (1995)); Kanaar et al., Trends Cell. Biol. 8: 483 (1998)). Although no such hydrolysis has been reported for covalent complexes between DNA and topoisomerase II or III, such hydrolysis has been described for covalent complexes between DNA and topoisomerase I (Yang et al., PNAS USA 93: 11534 (1996)).

The present invention seeks to provide the enzyme responsible for hydrolysis of the covalent complexes between DNA and topoisomerase I, specifically tyrosine-DNA phosphodiesterase, which acts on a tyrosine linked through the side-chain oxygen to the 3' phosphate of DNA. This and other objects and advantages, as well as additional inventive features, will become apparent to one of ordinary skill in the art from the detailed description provided herein.

BRIEF SUMMARY OF THE INVENTION

The present invention provides an isolated and purified nucleic acid molecule consisting essentially of a nucleotide sequence encoding a mammalian, in particular a human, tyrosine-DNA phosphodiesterase (TDP1) and a continuous fragment thereof of at least about 36 nucleotides. Also provided is an isolated or purified nucleic acid molecule encoding a modified mammalian TDP1, which comprises one or more insertions, deletions and/or substitutions, and a continuous fragment thereof of at least about 36 nucleotides. The modified mammalian TDP1 does not differ functionally from the corresponding unmodified mammalian TDP1.

An isolated and purified nucleic acid molecule consisting essentially of a nucleotide sequence encoding a yeast, in particular a *Saccharomyces cerevisiae*, TDP1 and a continuous fragment thereof comprising at least about 36 nucleotides are also provided by the present invention. In this regard, an isolated or purified nucleic acid molecule encoding a modified yeast TDP1, which comprises one or more insertions, deletions and/or substitutions, and a continuous fragment thereof of at least about 36 nucleotides, are also provided by the present invention. The modified yeast TDP1 does not differ functionally from the corresponding unmodified yeast TDP1.

The present invention further provides a vector comprising an above-described nucleic acid molecule and a vector comprising or encoding an antisense molecule of at least about 20 nucleotides that hybridizes to or a ribozyme that cleaves an RNA molecule encoding an above-described TDP1, as well as the antisense molecule and the ribozyme.

Also provided by the present invention is a host cell comprising an above-described vector, a polypeptide produced by such a host cell, and a polyclonal or monoclonal antibody that binds to an above-described TDP1.

Further provided by the present invention is a method of altering the level of TDP1 in a cell, a tissue, an organ or an organism. The method comprises contacting a cell, a tissue, an organ or an organism with a vector comprising a (i) a nucleic acid molecule encoding a TDP1, (ii) a nucleic acid molecule comprising or encoding an antisense molecule of at least about 20 nucleotides to an RNA molecule transcribed from (i), or (iii) a nucleic acid molecule comprising or encoding a ribozyme to an RNA molecule transcribed from (i). The vector comprising (i) increases or decreases the level of TDP1 in the cell, the tissue, the organ or the organism, whereas the vector comprising (ii) or (iii) decreases the level of TDP1 in the cell, the tissue, the organ or the organism. In this regard, the present invention also provides a cell, a tissue, an organ or a nonhuman organism in which the level of TDP1 has been altered in accordance with such a method.

Another method provided by the present invention is a method of identifying a compound that stabilizes a covalent bond complex that forms between DNA and topoisomerase I, wherein the covalent bond cannot be cleaved by or is resistant to cleavage by a TDP1. The method comprises (a) contacting a compound, which stabilizes a covalent bond complex that forms between DNA and topoisomerase I such that the covalent bond cannot be cleaved by or is resistant to cleavage by a TDP1, with DNA and topoisomerase I under conditions suitable for a covalent bond complex to form between the DNA and the topoisomerase I and for the compound to stabilize the covalent bond complex, (b) contacting the covalent bond complex with a TDP1 under conditions suitable for the cleavage of the covalent bond between the DNA and topoisomerase I by TDP1, and (c) detecting cleavage of the covalent bond by the TDP1. The amount of cleavage detected is indicative of whether or not the compound stabilizes a covalent bond complex that forms between DNA and topoisomerase I such that the covalent bond cannot be cleaved or is resistant to cleavage by the TDP1.

Yet another method provided by the present invention is a method of assessing TDP1 activity in an animal. The method comprises (a) obtaining a sample of a cellular extract from an animal, wherein the cellular extract comprises TDP1, and (b) measuring the level of TDP1 activity in the sample.

Still yet another method provided by the present invention is a method of assessing the efficacy of a topoisomerase I inhibitor. The method comprises (a) obtaining a sample of DNA to which is covalently bound topoisomerase I after contact with a topoisomerase I inhibitor, (b) contacting the sample with a TDP1 under conditions suitable for cleavage of the covalent bond between the DNA and the topoisomerase I by TDP1, and (c) measuring the amount of topoisomerase I that is cleaved from the DNA. The amount of topoisomerase I that is cleaved from the DNA is indicative of the efficacy of the topoisomerase I inhibitor.

BRIEF DESCRIPTION OF THE FIGURES

FIG. 1 is the cDNA sequence encoding a human TDP1 (SEQ ID NO: 1).

FIG. 2 is the deduced amino acid sequence (SEQ ID NO: 13) of the cDNA of FIG. 1. The start codon (M) is circled.

FIG. 3 is the genomic DNA sequence encoding a yeast TDP1 (SEQ ID NO: 3).

FIG. 4 is the deduced amino acid sequence (SEQ ID NO: 4) of the genomic DNA of FIG. 3.

FIG. 5 is an alignment of TDP1 homologs from various organisms, including human (SEQ ID NO: 5), mouse (SEQ ID NO: 6), *Drosophila melanogaster* (SEQ ID NO: 7), *Caenorhabditis elegans* (SEQ ID NO: 8), *Schitosaccharomyces pombe* (SEQ ID NO: 9), and *Saccharomyces cerevisiae* (SEQ ID NO: 4).

DETAILED DESCRIPTION OF THE INVENTION

In one embodiment, the present invention provides isolated or purified nucleic acid molecules. By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." "Nucleic acid molecules" is intended to encompass a polymer of DNA or RNA, i.e., a polynucleotide, which can be single-stranded or double-stranded and which can contain non-natural or altered nucleotides.

One isolated or purified nucleic acid molecule consists essentially of a nucleotide sequence encoding a mammalian TDP1 or a continuous fragment thereof of at least about 36 nucleotides. Preferably, the mammalian TDP1 is a human TDP1. Also, preferably, the mammalian TDP1 is (i) DNA and consists essentially of SEQ ID NO: 1 or a sequence that encodes SEQ ID NO: 2, (ii) RNA and consists essentially of a sequence encoded by SEQ ID NO: 1 or a sequence that encodes SEQ ID NO: 2, or (iii) a nucleic acid molecule consisting essentially of a nucleotide sequence that encodes a mammalian TDP1 or a continuous fragment of at least about 12 amino acids thereof and that hybridizes to either one of the foregoing under low stringency conditions.

Also provided is an isolated or purified nucleic acid molecule encoding a modified mammalian TDP1, which comprises one or more insertions, deletions and/or substitutions, wherein the modified mammalian TDP1 encoded by the isolated or purified nucleic acid molecule does not differ functionally from the corresponding unmodified mammalian TDP1, or a continuous fragment thereof of at least about 36 nucleotides. Desirably, the modified mammalian TDP1 does not differ functionally from the corresponding unmodified mammalian TDP1, such as that comprising SEQ ID NO: 2. Preferably, the modified mammalian TDP1 cleaves a covalent bond complex between DNA and topoisomerase I at least about 90% as well as the corresponding unmodified mammalian TDP1, such as that comprising SEQ ID NO: 2, as determined by in vitro assay using labeled topoisomerase I or an oligonucleotide comprising a 3' phosphotyrosine (see, e.g., Yang et al. (1996), supra). Use of the word "labeled" herein is intended to mean any means of detection, such as a radioactive isotope.

Another isolated or purified nucleic acid molecule consists essentially of a nucleotide sequence encoding a yeast TDP1 or a continuous fragment thereof comprising at least about 36 nucleotides. Preferably, the yeast TDP1 is a *Saccharomyces cerevisiae* TDP1. Also, preferably, the yeast TDP1 is (i) DNA and consists essentially of SEQ ID NO: 3 or a sequence that encodes SEQ ID NO: 4, (ii) RNA and consists essentially of a sequence encoded by SEQ ID NO: 3 or a sequence that encodes SEQ ID NO: 4, or (iii) a nucleic acid molecule consisting essentially of a nucleotide sequence that encodes a yeast TDP1 or a continuous fragment of at least about 12 amino acids thereof and that hybridizes to either one of the foregoing under low stringency conditions. Yeast TDP1 will act on a tyrosine linked through the side-chain oxygen to the 3' phosphate of single-stranded and double-stranded DNA.

Also provided is an isolated or purified nucleic acid molecule encoding a modified yeast TDP1, which comprises one or more insertions, deletions and/or substitutions, wherein the modified yeast TDP1 encoded by the isolated or purified nucleic acid molecule does not differ functionally from the corresponding unmodified yeast TDP1, or a continuous fragment thereof of at least about 36 nucleotides. Desirably, the modified yeast TDP1 does not differ functionally from the corresponding unmodified yeast TDP1, such as that comprising SEQ ID NO: 4. Preferably, the modified yeast TDP1 cleaves a covalent bond complex between DNA and topoisomerase I at least about 90% as well as the corresponding unmodified yeast TDP1, such as that comprising SEQ ID NO: 4, as determined by in vitro assay using labeled topoisomerase I or an oligonucleotide comprising a 3' phosphotyrosine.

With respect to the above, one of ordinary skill in the art knows how to generate insertions, deletions and/or substitutions in a given nucleic acid molecule. Also with respect to the above, "does not differ functionally from" is intended to mean that the modified enzyme has enzymatic activity characteristic of the unmodified enzyme. In other words, it acts upon the same substrate and generates the same product. The modified enzyme, however, can be more or less active than the unmodified enzyme as described in accordance with the present invention.

Nucleic acid molecules encoding TDP1 can be isolated from numerous eukaryotic sources. In this regard, TDP1 is highly conserved among eukaryotes. With respect to the above isolated or purified nucleic acid molecules, it is preferred that the one or more substitution(s) do(es) not result in a change in an amino acid of the enzyme. Alternatively, and also preferred, is that the one or more subsitution(s) result(s) in the substitution of an amino acid of the encoded yeast TDP1 with another amino acid of approximately equivalent size, shape and charge.

Also with respect to the above isolated or purified nucleic acid molecules, a "continuous fragment of at least about 36 nucleotides of the isolated or purified nucleic acid molecule," preferably encodes a polypeptide that can carry out the same function as the corresponding complete polypeptide or protein. For example, a fragment of an isolated or purified nucleic acid molecule encoding a mammalian TDP1 can be a continuous fragment of the TDP1-encoding nucleic acid molecule that encodes a polypeptide that can cleave a covalent bond complex between DNA and topoisomerase I, but not necessarily as well as the corresponding complete polypeptide or protein.

The above isolated or purified nucleic acid molecules also can be characterized in terms of "percentage of sequence identity." In this regard, a given nucleic acid molecule as described above can be compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison can be conducted by computerized implementations of known algorithms (e.g., GAP, BESTFIT, FASTA, and TFASTA in the Wisconsin Genetics Software Package Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that at least about 75%, preferably at least about 80%, more preferably at least about 90%, and most preferably at least about 95% of the sequence of a given nucleic acid molecule is identical to a given reference sequence or that at least about 40%, preferably at least about 60%, more preferably at least about 90%, and most preferably at least about 95% of the amino acids of which a given polypeptide is comprised are identical to or represent conservative substitutions of the amino acids of a given reference sequence.

Another indication that polynucleotide sequences are substantially identical is if two molecules selectively hybridize to each other under stringent conditions. The phrase "selectively hybridizing to" refers to the selective binding of a single-stranded nucleic acid probe to a single-stranded target DNA or RNA sequence of complementary sequence when the target sequence is present in a preparation of heterogeneous DNA and/or RNA. Stringent conditions are sequence-dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. "Low stringency conditions," as that term is used herein, means those conditions that allow for as much as about 80% mismatch.

The above-described nucleic acid molecules can be used, in whole or in part (i.e., as fragments), to identify and isolate corresponding genes from other eukaryotes for use in the context of the present inventive method using conventional means as known in the art. For example, such molecules or fragments thereof can be used in chromosome walking, genomic subtraction, which requires the availability of strains having deletions of the target gene (Strauss and Ausubel, PNAS USA 87: 1889–1893 (1990); and Sun et al., Plant Cell 4: 119–128 (1992)), transposon (Chuck et al., Plant Cell 5: 371–378 (1993); Dean et al., Plant J. 2: 69–81 (1992); Grevelding et al., PNAS USA 899: 6085–6089 (1992); Swinburne et al., Plant Cell 4: 583–595 (1992); Fedoroff and Smith, Plant J. 3: 273–289 (1993); and Tsay et al., Science 260: 342–344 (1993)) and T-DNA tagging (Feldmann, Plant J. 1: 71–82 (1991); Feldmann et al., Science 243: 1351–1354 (1989); Herman et al., Plant Cell 11: 1051–1055 (1989); Konz et al., EMBO J. 9: 1337–1346 (1989); and Kieber et al., Cell 72: 427–441 (1993)), and heterologous probe selection techniques in accordance with methods well-known in the art. Although T-DNA tagging, chromosome walking or heterologous probe selection can identify a DNA fragment that putatively contains the gene of interest, the DNA fragment must be confirmed by genetic complementation or some other means.

In another embodiment, the present invention also provides a vector comprising a nucleic acid molecule as described above. A nucleic acid molecule as described above can be cloned into any suitable vector and can be used to transform or transfect any suitable host cell, whether a single cell or a collection of cells, such as in the context of a tissue, an organ or an organism. The selection of vectors and methods to construct them are commonly known to persons of ordinary skill in the art and are described in general technical references (see, in general, "Recombinant DNA Part D," *Methods in Enzymology,* Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColEl, 2 mμ plasmid, λ, SV40, bovine papilloma virus, and the like.

Yeast centromeric plasmid (YCp50) constructs can be used to express TDP1 in yeast.

In addition to the replication system and the inserted nucleic acid, the construct can include one or more marker genes, which allow for selection of transformed or transfected hosts, if so desired. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λ GT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAM-neo (Clonetech, Palo Alto, Calif.). Other examples of suitable vectors include the yeast centromeric plasmid (YCp50), 2u and integrative vectors, such as the pRS series (Bachmann et al., Yeast 14: 115 (1998)) or PYES2 (Invitrogen).

An expression vector can comprise a native or nonnative promoter operably linked to a nucleic acid molecule encoding a TDP1 as described above. The selection of promoters, e.g., strong, weak, inducible, repressible, cell-specific, tissue-specific, organ-specific and developmental-specific, is within the skill in the art. Similarly, the combining of a nucleic acid molecule as described above with a promoter is also within the skill in the art.

The present invention not only provides a vector comprising a nucleic acid molecule as described above-but also provides a vector comprising or encoding an antisense molecule that hybridizes to or a ribozyme that cleaves an RNA molecule encoding a TDP1 as described above. The present invention also provides the antisense molecules and ribozymes, themselves.

Antisense nucleic acids can be generated in accordance with methods known in the art. The nucleic acid molecule introduced in antisense inhibition generally is substantially identical to at least a portion, preferably at least about 20 continuous nucleotides, of the nucleic acid to be inhibited, but need not be identical. The complex can, thus, be designed such that the inhibitory effect applies to other proteins within a family of genes exhibiting homology or substantial homology to the nucleic acid. The introduced sequence also need not be full-length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

The inclusion of ribozyme sequences within antisense RNAs confers RNA-cleaving activity upon them, thereby increasing the activity of the constructs. The design and use of target RNA-specific ribozymes is described in Haseloff et al., Nature 334: 585–591 (1988). Preferably, the ribozyme comprises at least about 20 continuous nucleotides complementary to the target sequence on each side of the active site of the ribozyme.

In view of the above, the present invention provides a host cell comprising a vector as vector as described above. In addition, the present invention provides a polypeptide produced by a host cell comprising a vector as described above.

Suitable hosts of cells include mammalian, such as human, and insect cells, yeast (e.g., S288c strain (wild-type) S. cerevisiae), and bacteria (e.g., E. coli strain BL21 (DE3)).

Also provided by the present invention is a purified and isolated mammalian, in particular human, TDP1. A mammalian, in particular a human, TDP1 can be purified and isolated using methods known to those of ordinary skill in the art. For example, a human, TDP1 can be isolated or purified by forming a human TDP1 fusion protein containing a polyhistidine tail and purifying via nickel-chelation chromatography.

In addition to the above, the present invention provides polyclonal and monoclonal antibodies to TDP1. Preferably, the antibody binds to a mammalian TDP1 but does not bind to a nonammalian TDP1 or the antibody binds to a yeast TDP1 but does not bind to a non-yeast TDP1. Methods of polyclonal and monoclonal antibody production are known in the art. See, for example, Harlow and Lane, in Antibodies. A Laboratory Manual. Cold Spring Harbor Laboratory, Cold Spring Harbor, 1988, pp. 1–725). For example, a yeast TDP fusion protein containing a polyhistidine tail was expressed in a bacterial expression vector and purified via nickel-chelation chromatography. Pure protein was isolated from bacterial cultures and injected into rabbits using standard methods to generate polyclonal antibodies. Antibodies were harvested ten weeks later and were shown to interact effectively with and to precipitate yeast TDP1.

In another embodiment, the present invention provides a method of altering the level of TDP1 in a cell, tissue, organ or organism. By "altering" is meant that the TDP1 level in a given cell, tissue, organ or organism is different as a result of the practice of the present inventive method as compared to a like cell, tissue, organ or organism in which the level of TDP1 has not been altered as a result of the practice of the present inventive method.

The method comprises contacting the cell, the tissue, the organ or the organism with a vector comprising a nucleic acid molecule selected from the group consisting of (i) a nucleic acid molecule encoding a TDP1, (ii) a nucleic acid molecule comprising or encoding an antisense sequence of at least about 20 nucleotides to an RNA molecule transcribed from (i), and (iii) a nucleic acid molecule comprising or encoding a ribozyme to an RNA molecule transcribed from (i). The vector comprising a nucleic acid molecule of (i) increases or decreases the level of TDP1 in the cell, the tissue, the organ or the organism, whereas the vector comprising a nucleic acid molecule of (ii) or (iii) decreases the level of TDP1 in the cell, the tissue, the organ or the organism. Accordingly, the present invention further provides a cell, a tissue, an organ or a nonhuman organism in which the level of TDP1 has been altered in accordance with the method.

By "contacting" is meant bringing the cell, tissue, organ or organism into sufficiently close proximity with the vector such that the vector is taken up by the cell or by cells in the tissue, organ or organism, wherein it can be expressed. The method is not dependent on any particular means of contact and is not to be so construed. Means of contact are well-known to those skilled in the art, and also are exemplified herein.

Accordingly, contact can be effected, for instance, either in vitro (e.g., in an ex vivo type method of gene therapy) or in vivo, which includes the use of electroporation, transformation, transduction, conjugation or triparental mating, transfection, infection, membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art.

Preferably, however, the vectors (including antisense molecules and ribozymes) are introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (e.g., as reviewed in PCT patent application no. WO 95/21259) can be employed in the present invention. For liposome administration, the recommendations identified in the PCT patent application No. WO 93/23569 can be followed. Generally, with such administration the formulation is taken up by the majority of lymphocytes within 8 hr at 37° C., with more than 50% of the injected dose being detected in the spleen an hour after intravenous administration. Similarly, other delivery vehicles include hydrogels and controlled-release polymers.

The form of the vector introduced into a host cell can vary, depending in part on whether the vector is being introduced in vitro or in vivo. For instance, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus, or stably introduced into the host genome through double or single crossover recombination events.

Preferably, the nucleic acid molecule used in the above-described method is one of those described above. In this regard, nucleic acid molecules that correspond to the above-described nucleic acid molecules but which have been isolated from other eukaryotic sources, in particular other mammalian or yeast sources, can be used in the context of the present inventive method to increase the level of TDP1 in a cell, tissue, organ or organism, provided that a cDNA sequence is used in those instances where the genomic sequence contains introns that may not be properly processed in a given cell, tissue, organ or organism. In addition, it may be necessary to alter the cDNA sequence so that it contains codon sequences that are preferred in a given species. However, to the extent that antisense or ribozyme sequences are employed in the present inventive method, it would be advantageous to use a nucleic acid molecule isolated from a eukaryotic source that is of the same origin as the cell, the tissue, the organ or the organism in which the level of TDP1 is to be altered.

If it is desired to increase the expression of TDP1, it is preferred to do so by introducing a gene encoding TDP1. Preferably, a vector comprising a nucleotide sequence encoding TDP1 operably linked to a promoter that is functional in the cell, the tissue, the organ or the organism with which it is brought into contact is used. It is preferred that either multiple extra copies of the gene are introduced into the cell, the tissue, the organ or the organism or that a vector comprising a strong promoter is introduced into the cell, the tissue, the organ or the organism such that the coding sequence is expressed at a higher rate, thereby generating more mRNA, which, in turn, is translated into more of the encoded enzyme.

In this regard, if expression is desired in a given cell, tissue or organ, a cell-, tissue- or organ specific promoter can be used in the vector. Developmentally specific promoters and regulatable, i.e., inducible or repressible, e.g., metallothionein promoter and radiation-responsive promoter, also can be used. Examples of such promoters, as well as enhancer elements and suppressor elements, are known in the art. Promoters can be found, for example, in eukaryotic promoter databases (see, e.g., the Eukaryotic Promoter Database of the Swiss Institute for Experimental Cancer Research (ISREC) (Epalinges, Switzerland) (available online through the Kyoto University Bioinformatics Center (GenomeNet) (Kyoto, Japan)) and other such databases.

In addition, a nucleic acid can be directly or indirectly linked to a targeting moiety. A "targeting moiety," such as that term is used herein is any molecule that can be linked with an above-described nucleic acid directly or indirectly, such as through a suitable delivery vehicle, such that the targeting moiety preferentially binds to a target cell as compared to a non-target cell. The targeting moiety can bind to a target cell through a receptor, a substrate, an antigenic determinant or another binding site on the target cell. Examples of a targeting moiety include an antibody (i.e., a polyclonal or a monoclonal antibody), an immunologically reactive fragment of an antibody, an engineered immunoprotein and the like, a protein (target is receptor, as substrate, or regulatory site on DNA or RNA), a polypeptide (target is receptor), a peptide (target is receptor), a nucleic acid, which is DNA or RNA (i.e., single-stranded or double-stranded, synthetic or isolated and purified from nature; target is complementary nucleic acid), a steroid (target is steroid receptor), and the like. In general, there are a number of databases for targeting moieties (see, e.g., the Kyoto Encyclopedia of Genes and Genomes (available online through the Kyoto University Bioinformatics Center (GenomeNet) (Kyoto, Japan)); Kanehisa, *Trends Genet.*, 13, 375–376 (1997); and Kanehisa, et al., Nucleic Acids Res., 28, 27–30 (2000)).

Analogs of targeting moieties that retain the ability to bind to a defined target also can be used. In addition, synthetic targeting moieties can be designed, such as to fit a particular epitope. Alternatively, the therapeutic nucleic acid can be encapsulated in a liposome comprising on its surface the targeting moiety.

The targeting moiety can include a linking group that can be used to join a targeting moiety to, in the context of the present invention, an above-described nucleic acid. It will be evident to one skilled in the art that a variety of linking groups, including bifunctional reagents, can be used. The targeting moiety can be linked to the nucleic acid by covalent or non-covalent bonding. If bonding is non-covalent, the conjugation can be through hydrogen bonding, ionic bonding, hydrophobic or van der Waals interactions, or any other appropriate type of binding.

If it is desired to decrease the expression of TDP1, it is preferred to do so by introducing either a nucleic acid molecule comprising (i.e., in the case of an RNA vector) or encoding (i.e., in the case of a DNA vector) an antisense nucleic acid molecule to an RNA molecule transcribed from an aforementioned gene or a nucleic acid molecule comprising a ribozyme to an RNA molecule transcribed from such a gene. In antisense technology, a nucleic acid segment from the desired gene can be cloned and operably linked to the promoter sequence such that the anti-sense strand of RNA is transcribed. Another alternative method to decrease TDP1 is to use a compound that inhibits the transcription, translation or activity of TDP1.

In addition to the above, gene replacement technology can be used to increase or decrease the expression of TDP1.

Gene replacement technology is based on homologous recombination. The nucleic acid of TDP1 can be manipulated by mutagenesis (e.g., insertions, deletions, duplications or replacements) to either increase or decrease its function. The altered sequence can be introduced into the genome to replace the existing, e.g., wild-type, gene via homologous recombination.

The activity of TDP1 can be measured using labeled substrates in vitro. TDP1 activity can be assay quickly and conveniently in vitro by mixing a radioactively 5'-labeled 18-mer oligonucleotide with a 3'phosphotyrosyl group and TDP1. The material is then run on a polyacrylamide sequencing gel and exposed to autoradiographic film. Product bands then can be quantitated (see Yang et al. (1996), supra). TDP1 will also act on thymidine 3'-nitrophenyl phosphate in vitro.

In addition to being useful in the study of TDP1, the above-described method is useful in the context of prophylactic and therapeutic treatment, such as chemotherapy, in particular where the chemotherapeutic agent is an inhibitor of topoisomerase I and causes the formation of DNA-topoisomerase I complexes that cannot be cleaved or are resistant to cleavage by TDP1, such as campothecin, topotecan and irinotecan (CPT-11) and analogs thereof (see, e.g., Slichenmyer et al., J. Natl. Cancer Inst. 85(4): 271–291 (1993); Slichenmyer et al., Cancer Chemother. Pharmacol. 34(Suppl.): S53–57 (1994); Burris & Fields, Hemtol. Onol. Clin. North Am. 8(2): 333–355 (1994); Hawkins, Oncology 6(12): 17–23 (1992); Emerson et al., Cancer Res. 55(3): 603–609 (1995); Sugimori et al., J. Med. Chem. 37(19): 3033–3039 (1994); Wall et al., J. Med. Chem. 36(18): 2689–2700 (1993); Kingsbury et al., J. Med. Chem. 34(1): 98–107 (1991); Wani et al., J. Med. Chem. 30(10): 1774–1779 (1987); Wani et al., J. Med. Chem. 23: 554–560 (1980); and Wani et al. (1986)). In this regard, a patient with low levels of TDP1 might be overly sensitive to compounds that inhibit topoisomerase I and might benefit from treatment with lower doses of topoisomerase I inhibitors or increased expression of TDP1. In contrast, a patient with high levels of TDP1 might be resistant to compounds that inhibit topoisomerase I and might benefit from treatment with higher doses of topoisomerase I inhibitors or reduced expression of TDP1.

In the context of chemotherapy and other methods of treatment, a topoisomerase I inhibitor and an above-described nucleic acid molecule can be administered simultaneously or sequentially in either order, by the same route of administration or by different routes of administration. In this regard, the topoisomerase I inhibitor and the above-described nucleic acid molecule can be present in a single biologically or pharmaceutically acceptable composition or in separate biologically or pharmaceutically acceptable compositions. Pharmaceutically acceptable compositions comprise pharmaceutically acceptable carriers and diluents as appropriate, for example, for human or veterinary applications, as are known in the art.

Thus, a composition for use in the method of the present invention can comprise an above-described nucleic acid molecule, e.g., vector, preferably in combination with a pharmaceutically acceptable carrier. Pharmaceutically acceptable carriers are well-known to those skilled in the art, as are suitable methods of administration. The choice of carrier will be determined, in part, by the particular nucleic acid molecule, as well as by the particular method used to administer the composition. One skilled in the art will also appreciate that various routes of administering a composition are available and, although more than one route can be used for administration, a particular route can provide a more immediate and more effective reaction than another route. Accordingly, there are a wide variety of suitable formulations of the composition of the present invention.

A composition comprised of a nucleic acid molecule of the present invention, alone or in combination with another active agent, such as a chemotherapeutic agent that inhibits topoisomerase I by causing formation of complexes between DNA and topoisomerase I that cannot-be cleaved or are resistant to cleavage by TDP1, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multidose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

An aerosol formulation suitable for administration via inhalation also can be made. The aerosol formulation can be placed into a pressurized acceptable propellant, such as dichlorodifluoromethane, propane, nitrogen, and the like.

Similarly, a formulation suitable for oral administration can include lozenge forms that can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

The dose administered to a mammal, particularly a human, in the context of the present invention should be sufficient to effect a therapeutic response in the infected individual over a reasonable time frame. The dose will be determined by the potency of the particular vector employed for treatment, the severity of the disease state, as well as the body weight and age of the infected individual. The size of the dose also will be determined by the existence of any adverse side effects that can accompany the use of the particular vector employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a vector, alone or in combination with other active agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient. Since the "effective level" is used as the preferred endpoint for dosing, the actual dose and schedule can vary, depending on interindividual differences in pharmacokinetics, drug distribution, and metabolism.

One skilled in the art can easily determine the appropriate dose, schedule, and method of administration for the exact formulation of the composition being used, in order to achieve the desired "effective level" in the individual patient. One skilled in the art also can readily determine and use an appropriate indicator of the "effective level" of the compounds of the present invention by a direct (e.g., analytical chemical analysis) or indirect analysis of appropriate patient samples (e.g., blood and/or tissues).

Generally, an amount of vector sufficient to achieve a tissue concentration of the administered ribozyme (or vector) of from about 50 to about 300 mg/kg of body weight per day is preferred, especially of from about 100 to about 200 mg/kg of body weight per day. In certain applications, e.g., topical, multiple daily doses are preferred. Moreover, the number of doses will vary depending on the means of delivery and the particular vector administered. In the treatment of some individuals, it can be desirable to utilize a "mega-dosing" regimen.

In yet another embodiment, the present invention provides a method of identifying a compound that stabilizes a covalent bond complex that forms between DNA and topoisomerase I such that the covalent bond cannot be cleaved by or is resistant to cleavage by a TDP1. The method comprises (a) contacting a compound, which stabilizes a covalent bond complex that forms between DNA and topoisomerase I such that the convalent bond cannot be cleaved by or is resistant to cleavage by a TDP1, with DNA and topoisomerase I under conditions suitable for a covalent bond complex to form between the DNA and the topoisomerase I and for the compound to stabilize the covalent bond complex, (b) contacting the covalent bond complex with a TDP1 under conditions suitable for cleavage of the covalent bond between the DNA and topoisomerase I by TDP1, and (c) detecting cleavage of the covalent bond by the TDP1. The amount of cleavage detected is indicative of whether or not the compound stabilizes a covalent bond complex that forms between DNA and topoisomerase I such that the covalent bond cannot be cleaved or is resistant to cleavage by the TDP1. For example, the more cleavage detected, the less the compound stabilizes a covalent bond complex that forms between DNA and topoisomerase I, and the less cleavage detected, the more the compound stabilizes a covalent bond complex that forms between DNA and topoisomerase I. Preferably, the compound is an analog of camptothecin, topotecan, or irinotecan (CPT- 11).

In still yet another embodiment, the present invention provides a method of assessing TDP1 activity in an animal. The method comprises (a) obtaining a sample of a cellular extract from an animal, wherein the cellular extract comprises TDP1, and (b) measuring the level of TDP1 activity in the sample. Assessing the level of TDP1 activity in a patient may be useful in predicting the patient's sensitivity to a topoisomerase I inhibitor, such as camptothecin, topotecan, irinotecan (CPT-11), an analog of any of the foregoing, and the like. For example, the more TDP1 activity a patient has, the less sensitive the patient will be to a topoisomerase I inhibitor, and the less TDP1 activity a patient has, the more sensitive the patient will be to a topoisomerase I inhibitor.

A still further embodiment of the present invention is a method of assessing the efficacy of a topoisomerase I inhibitor. The method comprises (a) obtaining a sample of DNA to which is covalently bound topoisomerase I after contact with a topoisomerase I inhibitor, (b) contacting the sample with a TDP1 under conditions suitable for cleavage of the covalent bond between the DNA and the topoisomerase I by TDP1, and (c) measuring the amount of topoisomerase I that is cleaved from the DNA. The amount of topoisomerase I that is cleaved from the DNA is indicative of the efficacy of the topoisomerase I inhibitor. Preferably, the sample of DNA is obtained from a patient undergoing treatment with the topoisomerase I inhibitor and the patient's dosage or frequency of administration of topoisomerase I is adjusted down or up based on the high or low efficacy, respectively, of the topoisomerase I inhibitor. Also, preferably, the sample is obtained from peripheral blood cells of the patient. This method can be adapted for screening potential environmental mutagens for DNA-topoisomerase I complexes that are noncleavable by or resistant to cleavage by TDP1.

With respect to the above three methods, methods of contacting a compound with DNA and an enzyme, the determination of conditions suitable for formation, stabilization and cleavage of a DNA —topoisomerase I covalent bond complex, such as physiological conditions, and the detection and measurement of enzyme activity, as well as the preparation of cellular extracts are within the skill in the art (see also, the paragraph bridging pages 5–6, the fourth full paragraph on page 11, and the Examples herein and Yang et al. (1996), supra).

EXAMPLES

The present invention is described further in the context of the following examples. These examples serve to illustrate further the present invention and are not intended to limits its scope in any way.

In the following examples using yeast, standard protocols of yeast growth, mutagenesis, mating and sporulation were used (see, e.g., Sherman, Methods Enzymol. 194:3 (1991); Treco and Lundblad, in *Current Protocols in Molecular Biology*, Ausubel et al., eds. (Wiley, N.Y. (1991)), vol. 2. pp. 13.1.1–13.1.7.).

Example 1

This example describes how the genomic DNA sequence of the yeast TDP1 gene was obtained.

Extracts from colonies of chemically mutagenized *Saccharomyces cervisiae* were assayed for TDP activity. A single strain, KYY337, had very low TDP activity. In backcrosses to the parental line, the enzyme defect appeared to reflect a single mutation (designated enz). That is, when a diploid between the parental line and a defective line was sporulated and haploid colonies were assayed at random, approximately equal numbers were found with normal and with low enzyme activity.

The strains were compared for sensitivity to killing by camptothecin. Despite the dramatic difference in TDP activity, the parental line and the backcrossed enz mutant were insensitive to camptothecin. When combined with a disruption of the RAD9 gene, the camptothecin sensitivity of the low activity mutant (strain HNY244) was increased by a factor of 12 relative to the rad9 derivative of the parental strain HNY243. The same difference was observed after the mutant had undergone two additional rounds of backcrossing. In order to confirm that camptothecin-induced damage was due to topoisomerase trapping, the TOP1 gene of HNY244 was disrupted and survival increased nearly 1,000-fold.

While the mutant line was sensitized to killing by camptothecin, the mutant line was not sensitized to all sources of DNA damage. For example, the mutant line was not sensitized to killing by methyl methane sulfonate, a DNA-alkylating agent. In addition, independent overexpression of two mutant yeast topoisomerase I genes that depress resealing of DNA, thereby leading to an accumulation of covalent complexes, were more toxic in a strain with low TDP activity than in a corresponding control strain.

In view of the above, a library of yeast genomic fragments was screened for the ability to improve the camptothecin resistance of HNY244 and restore its TDP activity. The cloning scheme was based on the assessment that (i) the signal:noise ratio of the TDP assay would permit detection of one positive colony in a group of 5–10 mutants and (ii) one cycle of camptothecin killing would enrich a positive colony by approximately ten-fold.

Strain HNY244 was transformed by electroporation with a genomic library that had been made in a low-copy number vector (Rose et al., Gene 60: 237 (1987)). Transformants were picked from uracil-selective plates and pooled in groups of about 50.

Each pool was separately grown and treated with camptothecin for 24 hours. Cells were grown to near-saturation in medium with glycerol in place of dextrose (YPG) to ensure a starting population with few or no petite derivatives in accordance with standard methods. These cells were resuspended at $OD_{650}$=0.4 in YPD (bacto-yeast extract, peptone and dextrose standard yeast growth medium), grown for 2 hrs and diluted again in YPD to $OD_{650}$=0.4. Drug was then added and samples were withdrawn immediately and after 24 hrs at 30° C. After dilution and plating on YPD, surviving colonies were counted after 3–4 days of growth. When plasmid-containing strains were assessed for camptothecin sensitivity, YPD was replaced throughout by uracil-deficient minimal medium to ensure plasmid retention. The survivors were amplified by growth in YPD.

An extract of an aliquot of the resulting cells was assayed for TDP activity. From 30 such pools, one was identified that had increased activity. Growth and assay of 15 colonies from this pool identified a single clone. L10–13, with nearly wild-type levels of activity. DNA sequence from the insert of the plasmid in L10–13 placed its centromere-distal end at coordinate 673926 of chromosome 11.

Several subclones of the approximately 8 kb insert in this plasmid were generated. Plasmid pNS2 was made from pL 10–13 by elimination of a NotI/SalI fragment. Elimination of an AatII-XbaI fragment from pNS2 yielded pAXb, which has a 3.2 kb insert. Several subclones retained full activity.

Transformation of HNY244 with pNS2 or pAXb restored TDP activity and improved camptothecin resistance. A control plasmid, pX1, that failed to restore TDP activity was made by removal of the central XbaI fragment from pL10–13.

The smallest subclone contained a single open reading frame (ORF), namely YBR223c, which encodes a protein of 544 amino acids with a molecular weight of about 62,000.

A disruption that removed all but the first 32 amino acids of the ORF was generated by PCR (Baudin, Nucleic Acids Res. 21: 3329 (1993); Ozier-Kalogeropoulos et al., Nucleic Acids Res. 21: 3329 (1993); Brachman et al., Yeast 14:115 (1998)) in strain HNY243. The resulting strain had an enzymatic defect and camptothecin sensitivity was very similar to that of HNY244, indicating that YBR223c is involved in TDP activity.

In order to distinguish whether YBR223c encodes or controls TDP activity, a histidine-tagged version of YBR223c was introduced into *E. coli,* which, by itself, has no detectable TDP activity. A PCR fragment containing the entire ORF YBR223c was cloned into the BamHI site of pET15b. The resulting plasmid, pHN1856, was transformed into strain BL21(DE3) (Novagen, Madison, Wis.). Bacterial pellets from 3 liters of a culture that had been induced for 2 hrs were resuspended in 100 ml of disruption buffer (Yang et al., PNAS USA 93: 11534 (1996)), sonicated (7×3 min), clarified by centrifugation at 20,000 g, and assayed as described above.

Induction of bacteria bearing this construct (but not a control construct) resulted in massive overproduction of TDP, since crude extracts of such cells had a specific activity greater than 10,000-fold higher than that of extracts from a standard yeast strain. Moreover, most of the induced activity was bound to a tag-specific column. Specific elution released more than 75% of the bound activity, resulting in a fraction with a single Coomasie-stainable band of the expected molecular size. Based on the above, it was concluded that YBR223c encodes TDP1.

Figure 5:
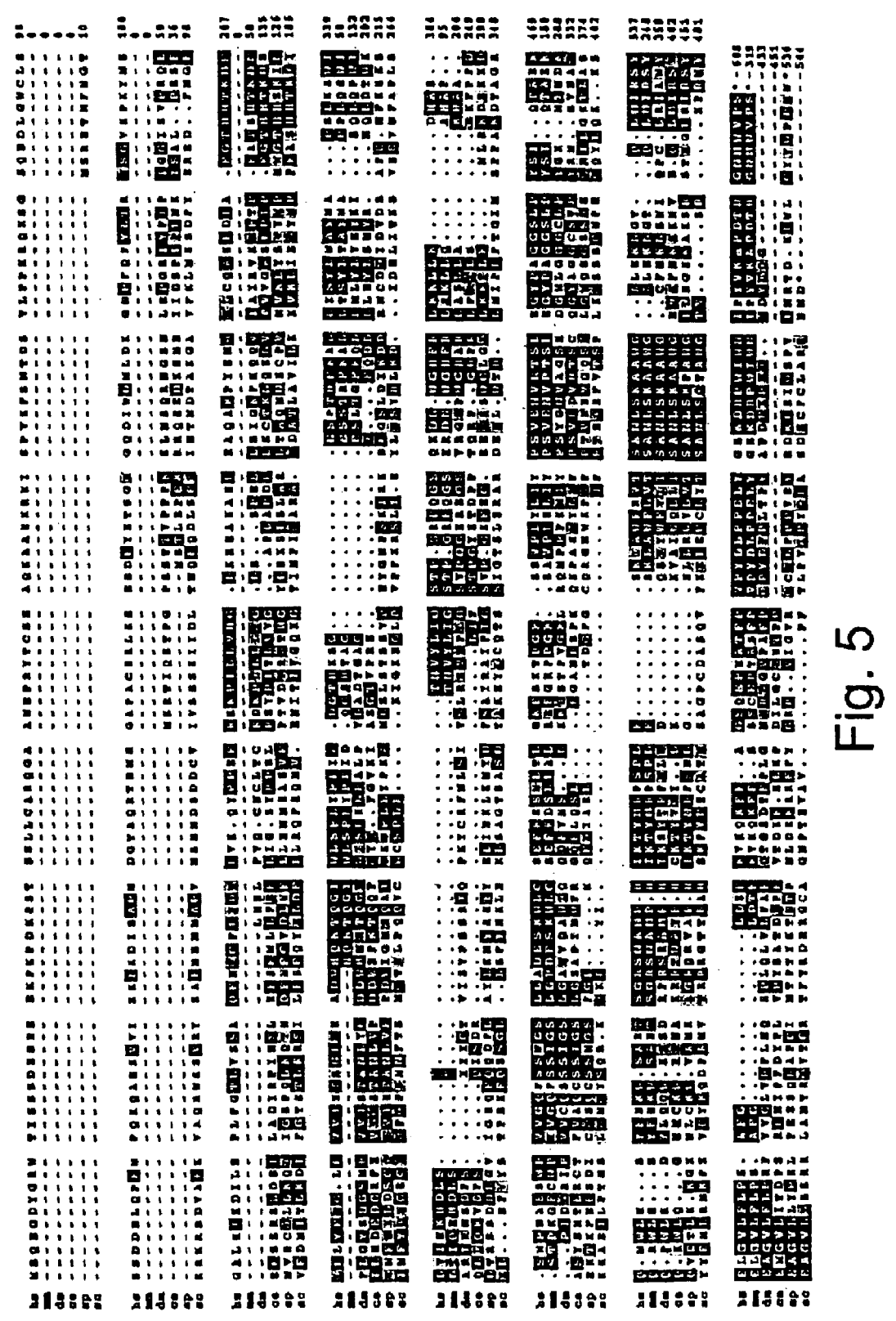

Database searches failed to reveal homology between TDP1 and any genes of known function. Even individualized comparisons to motifs identified in various phosphodiesterases and phosphatases were, at best, marginal. Thus, TDP1 encodes a novel enzyme. Eukaryotic databases contain several unannotated sequences that match TDP1. The complete genome sequence of the nematode *Caenorhabditis elegans* contains a single ORF with significant similarity to TDP1. Probing EST databases with the yeast and nematode proteins revealed many significant matches (see FIG. 5, which is an alignment of TDP homologs from various organisms, in which "hs" is the human deduced amino acid sequence (SEQ ID NO: 5), "mm" is the mouse amino acid sequence (*Mus muscularis;* assembly of mouse ESTs GenBank AA940134, W89267 and W13117) (SEQ ID NO: 6), "dm" is the fruit fly deduced amino acid sequence (*Drosophila melanogaster;* GenBank Al517253) (SEQ ID NO: 7), "ce" is the nematode deduced amino acid sequence (*Caenorhabditis elegans* (ce; gene F52C12.1; GenBank AF100657.2)) (SEQ ID NO: 8), "sp" is the *Schitosaccharomyces pombe* (Sanger Centre Sequencing Group (Cambridge, UK) deduced amino acid sequence (SEQ ID NO: 9), and "sc" is the yeast deduced amino acid sequence (*Saccharomyces cerevisiae;* gene YBR223c; GenBank Z36092.1) (SEQ ID NO: 4). Black boxes indicate identities, whereas shaded boxes indicate similarities and "x" indicates uncertainty in the GenBank entry AA48921. X's were confirmed by sequence analysis of the product of a 3' RACE of a human EST that showed that the sequence in the region of ambiguity is identical to that shown for the mouse).

Example 2

This example describes how the cDNA sequence of the human TDP1 gene was obtained.

A human database and a mouse EST database were searched with the yeast sequence and several EST's were identified that could be aligned to make up a single ORF with substantial similarity to the carboxy-terminal half of TDP1. In order to determine if the homology extends further, PCR was performed on a collection of human cDNAs (Marathon-Ready; Clontech Laboratories, Palo Alto, Calif.) with a primer complementary to an EST sequence identified in the human EST database and a primer complementary to the tag affixed to the 5' end of the cDNAs. The resulting 5'-RACE products were cloned. The sequence of one of the longest clones aligned well to most of the 5' half of the yeast and nematode ORFs. Based on the above, it was concluded that the TDP1 gene is highly conserved in eukaryotes.

Partial 5' and 3' sequences of the human TDP1 have been deposited as GenBank AF182002 and AF182003, respectively. The complete cDNA sequence (SEQ ID NO: 1) is shown in FIG. 1. The deduced amino acid sequence (SEQ ID NO: 13) is shown in FIG. 2.

All of the references cited herein, including patents, patent applications, and publications, are hereby incorporated in their entireties by reference.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. An isolated or purified nucleic acid molecule comprising SEQ ID NO: 1.

2. A vector comprising the nucleic acid molecule of claim 1.

3. An isolated host cell comprising the vector of claim 2.

4. An isolated or purified nucleic acid molecule comprising a nucleic acid sequence that is at least 95% identical to SEQ ID NO: 1 that encodes a polypeptide having tyrosine-DNA phosphodiesterase activity.

5. An isolated or purified nucleic acid molecule encoding the amino acid sequence of SEQ ID NO: 2.

6. An isolated or purified nucleic acid molecule having at least 95% sequence identity to the nucleic acid molecule of claim 5 and encoding a polypeptide having tyrosine-DNA phosphodiesterase activity.

7. An isolated or purified RNA molecule comprising a nucleic acid sequence transcribed from a nucleic acid sequence encoding the amino acid sequence of SEQ ID NO: 2.

8. The isolated or purified RNA molecule of claim 7, wherein the nucleic acid sequence is transcribed from SEQ ID NO: 1.

9. A vector comprising the RNA molecule of claim 7.

10. An isolated host cell comprising the vector of claim 9.

11. An isolated or purified nucleic acid molecule consisting of a continuous fragment of SEQ ID NO: 1, wherein said fragment encodes a polypeptide having tyrosine-DNA phosphodiesterase activity.

12. A vector comprising the nucleic acid molecule of claim 11.

13. An isolated host cell comprising the vector of claim 12.

14. The isolated or purified nucleic acid molecule of claim 11, wherein the nucleic acid molecule encodes the amino acid sequence of SEQ ID NO: 2.

* * * * *

SEQUENCE LISTING

<160> NUMBER OF SEQ ID NOS: 13

<210> SEQ ID NO 1
<211> LENGTH: 2091
<212> TYPE: DNA
<213> ORGANISM: Homo sapiens

<400> SEQUENCE: 1

```
ccgaggcaag cgttggttct gtgcgcctca ggagtataat gtctcaggaa ggcgattatg      60
ggaggtggac catatctagt agtgatgaaa gtgaggaaga aaagccaaaa ccagacaagc     120
catctacctc ttctcttctc tgtgccaggc aaggagcagc aaatgagccc aggtacacct     180
gttccgaggc ccagaaagct gcacacaaga ggaaaatatc acctgtgaaa ttcagcaata     240
cagattcagt tttacctccc aaaaggcaga aaagcggttc ccaggaggac ctcggctggt     300
gtctgtccag cagtgatgat gagctgcaac cagaaatgcc gcagaagcag gctgagaaag     360
tggtgatcaa aaaggagaaa gacatctctg ctcccaatga cggcactgcc caaagaactg     420
aaaatcatgg cgctcccgcc tgccacaggc tcaaagagga ggaagacgag tatgagacat     480
caggggaggg ccaggacatt tgggacatgc tggataaagg gaaccccttc cagttttacc     540
tcactagagt ctctggagtt aagccaaagt ataactctgg agccctccac atcaaggata     600
ttttatctcc tttatttggg acgcttgttt cttcagctca gtttaactac tgctttgacg     660
tggactggct cgtaaaacag tatccaccag agttcaggaa gaagccaatc ctgcttgtgc     720
atggtgataa gcgagaggct aaggctcacc tccatgccca ggccaagcct tacgagaaca     780
tctctctctg ccaggcaaag ttggatattg cgtttggaac acaccacacg aaaatgatgc     840
tgctgctcta tgaagaaggc ctccgggttg tcatacacac ctccaacctc atccatgctg     900
actggcacca gaaaactcaa ggaatatggt tgagcccctt atacccacga attgctgatg     960
gaacccacaa atctggagag tcgccaacac attttaaagc tgatctcatc agttacttga    1020
tggcttataa tgccccttct ctcaaggagt ggatagatgt cattcacaag cacgatctct    1080
ctgaaacaaa tgtttatctt attggttcaa ccccaggacg ctttcaagga agtcaaaaag    1140
ataattgggg acattttaga cttaagaagc ttctgaaaga ccatgcctca tccatgccta    1200
acgcagagtc ctggcctgtc gtaggtcagt tttcaagcgt tggctccttg ggagccgatg    1260
aatcaaagtg gttatgttct gagtttaaag agagcatgct gacactgggg aaggaaagca    1320
agactccagg aaaaagctct gttcctcttt acttgatcta tccttctgtg gaaaatgtgc    1380
```

```
ggaccagttt agaaggatat cctgctgggg gctctcttcc ctatagcatc cagacagctg    1440
aaaaacagaa ttggctgcat tcctatttc acaaatggtc agctgagact tctggccgca    1500
gcaatgccat gccacatatt aagacatata tgaggcctc tccagacttc agtaaaattg    1560
cttggttccg tgtcacaagc gcaaatctgt ccaaggctgc ctggggagca ttggagaaga    1620
atggcaccca gctgatgatc cgctcctacg agctcggggt cctttcctc ccttcagcat    1680 ttggtctaga cagtttcaaa gtgaaacaga agttcttcgc tggcagccag gagccaatgg    1740
ccacctttcc tgtgccatat gatttgcctc cagaactgta tggaagtaaa gatcggccat    1800
ggatatggaa cattccttat gtcaaagcac cggatacgca tgggaacatg tgggtgccct    1860
cctgagaatc ttgaggcact gtgaaattta agtgtaagac attgagccac aaacatggaa    1920
tctcttcttt gtactggatg tccacttccc ttaaagtctt atttgcaccc ttacaaaatc    1980
tttccaaagg tcactcttat gaatggatgt tggttatact tttaatggac attaacattc    2040
ctaataaagt attagtttct taaaaaaaaa aaaaaaaaaa aaaaaaaaa a              2091
```

<210> SEQ ID NO 2
<211> LENGTH: 620
<212> TYPE: PRT
<213> ORGANISM: Homo sapiens
<220> FEATURE:
<221> NAME/KEY: misc_feature
<223> OTHER INFORMATION: Amino acids 1-620 of the deduced amino acid
sequence of a human cDNA encoding TDP1

<400> SEQUENCE: 2

```
Glu Ala Ser Val Gly Ser Val Arg Leu Arg Ser Ile Met Ser Gln Glu
1               5                   10                  15

Gly Asp Tyr Gly Arg Trp Thr Ile Ser Ser Asp Glu Ser Glu Glu
            20                  25                  30

Glu Lys Pro Lys Pro Asp Lys Pro Ser Thr Ser Ser Leu Leu Cys Ala
        35                  40                  45

Arg Gln Gly Ala Ala Asn Glu Pro Arg Tyr Thr Cys Ser Glu Ala Gln
    50                  55                  60

Lys Ala Ala His Lys Arg Lys Ile Ser Pro Val Lys Phe Ser Asn Thr
65                  70                  75                  80

Asp Ser Val Leu Pro Pro Lys Arg Gln Lys Ser Gly Ser Gln Glu Asp
                85                  90                  95

Leu Gly Trp Cys Leu Ser Ser Ser Asp Asp Glu Leu Gln Pro Glu Met
            100                 105                 110

Pro Gln Lys Gln Ala Glu Lys Val Val Ile Lys Lys Glu Lys Asp Ile
        115                 120                 125

Ser Ala Pro Asn Asp Gly Thr Ala Gln Arg Thr Glu Asn His Gly Ala
    130                 135                 140

Pro Ala Cys His Arg Leu Lys Glu Glu Asp Glu Tyr Glu Thr Ser
145                 150                 155                 160

Gly Glu Gly Gln Asp Ile Trp Asp Met Leu Asp Lys Gly Asn Pro Phe
                165                 170                 175

Gln Phe Tyr Leu Thr Arg Val Ser Gly Val Lys Pro Lys Tyr Asn Ser
            180                 185                 190

Gly Ala Leu His Ile Lys Asp Ile Leu Ser Pro Leu Phe Gly Thr Leu
        195                 200                 205

Val Ser Ser Ala Gln Phe Asn Tyr Cys Phe Asp Val Asp Trp Leu Val
    210                 215                 220
```

```
Lys Gln Tyr Pro Pro Glu Phe Arg Lys Lys Pro Ile Leu Leu Val His
225                 230                 235                 240

Gly Asp Lys Arg Glu Ala Lys Ala His Leu His Ala Gln Ala Lys Pro
            245                 250                 255

Tyr Glu Asn Ile Ser Leu Cys Gln Ala Lys Leu Asp Ile Ala Phe Gly
                260                 265                 270

Thr His His Thr Lys Met Met Leu Leu Leu Tyr Glu Glu Gly Leu Arg
            275                 280                 285

Val Val Ile His Thr Ser Asn Leu Ile His Ala Asp Trp His Gln Lys
        290                 295                 300

Thr Gln Gly Ile Trp Leu Ser Pro Leu Tyr Pro Arg Ile Ala Asp Gly
305                 310                 315                 320

Thr His Lys Ser Gly Glu Ser Pro Thr His Phe Lys Ala Asp Leu Ile
                325                 330                 335

Ser Tyr Leu Met Ala Tyr Asn Ala Pro Ser Leu Lys Glu Trp Ile Asp
                340                 345                 350

Val Ile His Lys His Asp Leu Ser Glu Thr Asn Val Tyr Leu Ile Gly
            355                 360                 365

Ser Thr Pro Gly Arg Phe Gln Gly Ser Gln Lys Asp Asn Trp Gly His
370                 375                 380

Phe Arg Leu Lys Lys Leu Leu Lys Asp His Ala Ser Ser Met Pro Asn
385                 390                 395                 400

Ala Glu Ser Trp Pro Val Val Gly Gln Phe Ser Ser Val Gly Ser Leu
                405                 410                 415

Gly Ala Asp Glu Ser Lys Trp Leu Cys Ser Glu Phe Lys Glu Ser Met
                420                 425                 430

Leu Thr Leu Gly Lys Glu Ser Lys Thr Pro Gly Lys Ser Ser Val Pro
            435                 440                 445

Leu Tyr Leu Ile Tyr Pro Ser Val Glu Asn Val Arg Thr Ser Leu Glu
        450                 455                 460

Gly Tyr Pro Ala Gly Gly Ser Leu Pro Tyr Ser Ile Gln Thr Ala Glu
465                 470                 475                 480

Lys Gln Asn Trp Leu His Ser Tyr Phe His Lys Trp Ser Ala Glu Thr
                485                 490                 495

Ser Gly Arg Ser Asn Ala Met Pro His Ile Lys Thr Tyr Met Arg Pro
                500                 505                 510

Ser Pro Asp Phe Ser Lys Ile Ala Trp Phe Arg Val Thr Ser Ala Asn
            515                 520                 525

Leu Ser Lys Ala Ala Trp Gly Ala Leu Glu Lys Asn Gly Thr Gln Leu
        530                 535                 540

Met Ile Arg Ser Tyr Glu Leu Gly Val Leu Phe Leu Pro Ser Ala Phe
545                 550                 555                 560

Gly Leu Asp Ser Phe Lys Val Lys Gln Lys Phe Phe Ala Gly Ser Gln
                565                 570                 575

Glu Pro Met Ala Thr Phe Pro Val Pro Tyr Asp Leu Pro Pro Glu Leu
                580                 585                 590

Tyr Gly Ser Lys Asp Arg Pro Trp Ile Trp Asn Ile Pro Tyr Val Lys
            595                 600                 605

Ala Pro Asp Thr His Gly Asn Met Trp Val Pro Ser
610                 615                 620

<210> SEQ ID NO 3
<211> LENGTH: 1635
<212> TYPE: DNA
```

<213> ORGANISM: Saccharomyces cerevisiae

<400> SEQUENCE: 3

| | | | | | |
|---|---|---|---|---|---|
| atgtcacgag | aaacaaattt | caatggaact | aagaggaaga | ggtcggatgt | tgccgagaaa | 60 |
| gtagcacaac | ggtggaagag | cgtcaggtat | agtgctgaaa | tggagaatat | ggctccggtc | 120 |
| aacagtaaca | atgatagcga | cgactgcgtc | atagtcagtg | aatcgaaaat | cattgatttg | 180 |
| actaatcagg | aacaagattt | gagtgagaga | atagaaacaa | cgatacggc | aaaaggtgcc | 240 |
| gtttttaaac | taatgaaatc | ggacttctat | gaaagagagg | attttatggg | agaagtagag | 300 |
| gatatgatta | cattgaaaga | tatctttggc | actgagacac | taaaaagaag | catactcttc | 360 |
| agtttccaat | acgaacttga | tttcttgttg | agacaattcc | accagaacgt | agagaacata | 420 |
| accatcgtcg | gccaaaaggg | tactattatg | cctatcgaag | cccgtgctat | ggacgcgaca | 480 |
| ctggcagtaa | tattaaaaaa | ggtcaaactt | attgaaataa | cgatgccccc | attcgcttcc | 540 |
| caccatacga | agctgatcat | aaacttttac | gataatggcg | aatgcaaaat | attcttgcca | 600 |
| tctaacaatt | ttacgtcaat | ggagactaac | ctgcctcaac | aggtgtgttg | gtgcagtccc | 660 |
| cttttgaaaa | taggtaaaga | agggctacca | gtaccgttta | agagaagctt | gatagaatac | 720 |
| ctcaattcgt | accacctgaa | agacattgac | gaattgatta | caaaaagcgt | agaggaagtt | 780 |
| aactttgctc | ctttgagcga | attagaattt | gtatattcta | cgccctccaa | atttcagtcg | 840 |
| tcgggtttac | tgtcgtttta | caataaacta | gaaaaacttt | ctgctggcac | aagtgctagt | 900 |
| gatactgcaa | acattatct | atgtcaaact | tcatccatag | ggacatctct | atcaagagcg | 960 |
| cgagacgaaa | acttatggac | acatctaatg | attcctctgt | ttaccggaat | catgtcccct | 1020 |
| ccagcaaagg | acaccgctgg | gaggaagaaa | gcagaaatac | tgccaacgaa | ttcattgatt | 1080 |
| aatgaatatt | cgcagagaaa | aatcaagccg | tacattattt | tccccaccga | acaagagttt | 1140 |
| gtcaccagtc | ccttaaagtg | gtccagttcc | gggtggtttc | attttcaata | tcttcagaaa | 1200 |
| aagagctact | acgaaatgct | gcgaaacaag | ttcaaagtat | tttacaagca | agaccctgct | 1260 |
| atggttacta | gaagacgagg | gacgacgccc | gcgcactcta | agttttacat | gcattgtgca | 1320 |
| acaaactccg | cagggccctg | tgatgcatcg | caggtattta | agaactaga | atggtgcctt | 1380 |
| tatacttcgg | caaaccctcag | ccaaacagca | tggggcaccg | tttcaagaaa | accacgcaat | 1440 |
| tatgaagcag | gagtgcttta | ccatagtcgc | aggttagcaa | ataccaggaa | ggtcacgtgc | 1500 |
| cgtactttta | cacgtgaccg | tagaggctgc | gcgggtaatc | ccacccatgt | ggccgtgcca | 1560 |
| ttcacgctgc | cagtcatacc | atacgactta | gctgaggacg | agtgcttttg | ccttgctcgt | 1620 |
| catgagaacg | actaa | | | | | 1635 |

<210> SEQ ID NO 4
<211> LENGTH: 544
<212> TYPE: PRT
<213> ORGANISM: Saccharomyces cerevisiae

<400> SEQUENCE: 4

Met Ser Arg Glu Thr Asn Phe Asn Gly Thr Lys Arg Lys Arg Ser Asp
1               5                   10                  15

Val Ala Glu Lys Val Ala Gln Arg Trp Lys Ser Val Arg Tyr Ser Ala
            20                  25                  30

Glu Met Glu Asn Met Ala Pro Val Asn Ser Asn Asn Asp Ser Asp Asp
        35                  40                  45

Cys Val Ile Val Ser Glu Ser Lys Ile Ile Asp Leu Thr Asn Gln Glu
    50                  55                  60

```
Gln Asp Leu Ser Glu Arg Ile Glu Thr Asn Asp Thr Ala Lys Gly Ala
 65                  70                  75                  80

Val Phe Lys Leu Met Lys Ser Asp Phe Tyr Glu Arg Glu Asp Phe Met
             85                  90                  95

Gly Glu Val Glu Asp Met Ile Thr Leu Lys Asp Ile Phe Gly Thr Glu
            100                 105                 110

Thr Leu Lys Arg Ser Ile Leu Phe Ser Phe Gln Tyr Glu Leu Asp Phe
            115                 120                 125

Leu Leu Arg Gln Phe His Gln Asn Val Glu Asn Ile Thr Ile Val Gly
        130                 135                 140

Gln Lys Gly Thr Ile Met Pro Ile Glu Ala Arg Ala Met Asp Ala Thr
145                 150                 155                 160

Leu Ala Val Ile Leu Lys Lys Val Lys Leu Ile Glu Ile Thr Met Pro
                165                 170                 175

Pro Phe Ala Ser His His Thr Lys Leu Ile Ile Asn Phe Tyr Asp Asn
            180                 185                 190

Gly Glu Cys Lys Ile Phe Leu Pro Ser Asn Asn Phe Thr Ser Met Glu
            195                 200                 205

Thr Asn Leu Pro Gln Gln Val Cys Trp Cys Ser Pro Leu Leu Lys Ile
210                 215                 220

Gly Lys Glu Gly Leu Pro Val Pro Phe Lys Arg Ser Leu Ile Glu Tyr
225                 230                 235                 240

Leu Asn Ser Tyr His Leu Lys Asp Ile Asp Glu Leu Ile Thr Lys Ser
                245                 250                 255

Val Glu Glu Val Asn Phe Ala Pro Leu Ser Glu Leu Glu Phe Val Tyr
            260                 265                 270

Ser Thr Pro Ser Lys Phe Gln Ser Ser Gly Leu Leu Ser Phe Tyr Asn
            275                 280                 285

Lys Leu Glu Lys Leu Ser Ala Gly Thr Ser Ala Ser Asp Thr Ala Lys
        290                 295                 300

His Tyr Leu Cys Gln Thr Ser Ser Ile Gly Thr Ser Leu Ser Arg Ala
305                 310                 315                 320

Arg Asp Glu Asn Leu Trp Thr His Leu Met Ile Pro Leu Phe Thr Gly
                325                 330                 335

Ile Met Ser Pro Pro Ala Lys Asp Thr Ala Gly Arg Lys Lys Ala Glu
            340                 345                 350

Ile Leu Pro Thr Asn Ser Leu Ile Asn Glu Tyr Ser Gln Arg Lys Ile
            355                 360                 365

Lys Pro Tyr Ile Ile Phe Pro Thr Glu Gln Glu Phe Val Thr Ser Pro
370                 375                 380

Leu Lys Trp Ser Ser Ser Gly Trp Phe His Phe Gln Tyr Leu Gln Lys
385                 390                 395                 400

Lys Ser Tyr Tyr Glu Met Leu Arg Asn Lys Phe Lys Val Phe Tyr Lys
                405                 410                 415

Gln Asp Pro Ala Met Val Thr Arg Arg Arg Gly Thr Thr Pro Ala His
            420                 425                 430

Ser Lys Phe Tyr Met His Cys Ala Thr Asn Ser Ala Gly Pro Cys Asp
        435                 440                 445

Ala Ser Gln Val Phe Lys Glu Leu Glu Trp Cys Leu Tyr Thr Ser Ala
        450                 455                 460

Asn Leu Ser Gln Thr Ala Trp Gly Thr Val Ser Arg Lys Pro Arg Asn
465                 470                 475                 480
```

-continued

```
Tyr Glu Ala Gly Val Leu Tyr His Ser Arg Arg Leu Ala Asn Thr Arg
                485                 490                 495

Lys Val Thr Cys Arg Thr Phe Thr Arg Asp Arg Arg Gly Cys Ala Gly
            500                 505                 510

Asn Pro Thr His Val Ala Val Pro Phe Thr Leu Pro Val Ile Pro Tyr
        515                 520                 525

Asp Leu Ala Glu Asp Glu Cys Phe Cys Leu Ala Arg His Glu Asn Asp
    530                 535                 540

<210> SEQ ID NO 5
<211> LENGTH: 608
<212> TYPE: PRT
<213> ORGANISM: Homo sapiens

<400> SEQUENCE: 5

Met Ser Gln Glu Gly Asp Tyr Gly Arg Trp Thr Ile Ser Ser Ser Asp
1               5                   10                  15

Glu Ser Glu Glu Glu Lys Pro Lys Pro Asp Lys Pro Ser Thr Ser Ser
                20                  25                  30

Leu Leu Cys Ala Arg Gln Gly Ala Ala Asn Glu Pro Arg Tyr Thr Cys
            35                  40                  45

Ser Glu Ala Gln Lys Ala Ala His Lys Arg Lys Ile Ser Pro Val Lys
        50                  55                  60

Phe Ser Asn Thr Asp Ser Val Leu Pro Pro Lys Arg Gln Lys Ser Gly
65                  70                  75                  80

Ser Gln Glu Asp Leu Gly Trp Cys Leu Ser Ser Asp Asp Glu Leu
                85                  90                  95

Gln Pro Glu Met Pro Gln Lys Gln Ala Glu Lys Val Val Ile Lys Lys
            100                 105                 110

Glu Lys Asp Ile Ser Ala Pro Asn Asp Gly Thr Ala Gln Arg Thr Glu
        115                 120                 125

Asn His Gly Ala Pro Ala Cys His Arg Leu Lys Glu Glu Asp Glu
    130                 135                 140

Tyr Glu Thr Ser Gly Glu Gly Gln Asp Ile Trp Asp Met Leu Asp Lys
145                 150                 155                 160

Gly Asn Pro Phe Gln Phe Tyr Leu Thr Arg Val Ser Gly Val Lys Pro
                165                 170                 175

Lys Tyr Asn Ser Gly Ala Leu His Ile Lys Asp Ile Leu Ser Pro Leu
            180                 185                 190

Phe Gly Thr Leu Val Ser Ser Ala Gln Phe Asn Tyr Cys Phe Asp Val
        195                 200                 205

Asp Trp Leu Val Lys Gln Tyr Pro Pro Glu Phe Arg Lys Lys Pro Ile
    210                 215                 220

Leu Leu Val His Gly Asp Lys Arg Glu Ala Lys Ala His Leu His Ala
225                 230                 235                 240

Gln Ala Lys Pro Tyr Glu Asn Ile Ser Leu Cys Gln Ala Lys Leu Asp
                245                 250                 255

Ile Ala Phe Gly Thr His His Thr Lys Met Met Leu Leu Tyr Glu
            260                 265                 270

Glu Gly Leu Arg Val Val Ile His Thr Ser Asn Leu Ile His Ala Asp
        275                 280                 285

Trp His Gln Lys Thr Gln Gly Ile Trp Leu Ser Pro Leu Tyr Pro Arg
    290                 295                 300

Ile Ala Asp Gly Thr His Lys Ser Gly Glu Ser Pro Thr His Phe Lys
305                 310                 315                 320
```

```
Ala Asp Leu Ile Ser Tyr Leu Met Ala Tyr Asn Ala Pro Ser Leu Lys
            325                 330                 335

Glu Trp Ile Asp Val Ile His Lys His Asp Leu Ser Glu Thr Asn Val
            340                 345                 350

Tyr Leu Ile Gly Ser Thr Pro Gly Arg Phe Gln Gly Ser Gln Lys Asp
            355                 360                 365

Asn Trp Gly His Phe Arg Leu Lys Lys Leu Leu Lys Asp His Ala Ser
            370                 375             380

Ser Met Pro Asn Ala Glu Ser Trp Pro Val Val Gly Gln Phe Ser Ser
385                 390                 395                 400

Val Gly Ser Leu Gly Ala Asp Glu Ser Lys Trp Leu Cys Ser Glu Phe
            405                 410                 415

Lys Glu Ser Met Leu Thr Leu Gly Lys Glu Ser Lys Thr Pro Gly Lys
            420                 425                 430

Ser Ser Val Pro Leu Tyr Leu Ile Tyr Pro Ser Val Glu Asn Val Arg
            435                 440                 445

Thr Ser Leu Glu Gly Tyr Pro Ala Gly Gly Ser Leu Pro Tyr Ser Ile
    450                 455                 460

Gln Thr Ala Glu Lys Gln Asn Trp Leu His Ser Tyr Phe His Lys Trp
465                 470                 475                 480

Ser Ala Glu Thr Ser Gly Arg Ser Asn Ala Met Pro His Ile Lys Thr
                485                 490                 495

Tyr Met Arg Pro Ser Pro Asp Phe Ser Lys Ile Ala Trp Phe Arg Val
                500                 505                 510

Thr Ser Ala Asn Leu Ser Lys Ala Ala Trp Gly Ala Leu Glu Lys Asn
            515                 520                 525

Gly Thr Gln Leu Met Ile Arg Ser Tyr Glu Leu Gly Val Leu Phe Leu
    530                 535                 540

Pro Ser Ala Phe Gly Leu Asp Ser Phe Lys Val Lys Gln Lys Phe Phe
545                 550                 555                 560

Ala Gly Ser Gln Glu Pro Met Ala Thr Phe Pro Val Pro Tyr Asp Leu
                565                 570                 575

Pro Pro Glu Leu Tyr Gly Ser Lys Asp Arg Pro Trp Ile Trp Asn Ile
            580                 585                 590

Pro Tyr Val Lys Ala Pro Asp Thr His Gly Asn Met Trp Val Pro Ser
            595                 600                 605

<210> SEQ ID NO 6
<211> LENGTH: 319
<212> TYPE: PRT
<213> ORGANISM: Mus musculus

<400> SEQUENCE: 6

His Gln Lys Thr Gln Gly Ile Trp Leu Ser Pro Leu Tyr Pro Arg Ile
1               5                   10                  15

Asp Gln Gly Ser His Thr Ala Gly Glu Ser Ser Thr Arg Phe Lys Ala
            20                  25                  30

Asp Leu Thr Ser Tyr Leu Thr Ala Tyr Asn Ala Pro Pro Leu Gln Glu
        35                  40                  45

Trp Ile Asp Ile Ile Gln Glu His Asp Leu Ser Glu Thr Asn Val Tyr
    50                  55                  60

Leu Ile Gly Ser Thr Pro Gly Arg Phe Gln Gly Ser His Arg Asp Asn
65                  70                  75                  80

Trp Gly His Phe Arg Leu Arg Lys Leu Leu Gln Ala His Ala Pro Ser
```

```
                   85                  90                  95
Thr Pro Lys Gly Glu Cys Trp Pro Ile Val Gly Gln Phe Ser Ser Ile
            100                 105                 110

Gly Ser Leu Gly Pro Asp Glu Ser Lys Trp Leu Cys Ser Glu Phe Lys
            115                 120                 125

Asp Ser Leu Leu Ala Leu Arg Glu Glu Gly Arg Pro Pro Gly Lys Ser
130                 135                 140

Ala Val Pro Leu His Leu Ile Tyr Pro Ser Val Glu Asn Val Arg Thr
145                 150                 155                 160

Ser Leu Glu Gly Tyr Pro Ala Gly Gly Ser Leu Pro Tyr Ser Ile Gln
                165                 170                 175

Thr Ala Glu Lys Gln Arg Trp Leu His Ser Tyr Phe His Lys Trp Ser
            180                 185                 190

Ala Glu Thr Ser Gly Arg Ser Asn Ala Met Pro His Ile Lys Thr Tyr
                195                 200                 205

Met Arg Pro Ser Pro Asp Phe Ser Lys Leu Ala Trp Phe Leu Val Thr
            210                 215                 220

Ser Ala Asn Leu Ser Lys Ala Ala Trp Gly Ala Leu Glu Lys Asn Gly
225                 230                 235                 240

Thr Gln Leu Met Ile Arg Ser Tyr Glu Leu Gly Val Leu Phe Leu Pro
                245                 250                 255

Ser Ala Phe Gly Leu Asp Thr Phe Lys Val Lys Gln Lys Phe Phe Ser
            260                 265                 270

Ser Ser Cys Glu Pro Thr Ala Ser Phe Pro Val Pro Tyr Asp Leu Pro
            275                 280                 285

Pro Glu Leu Tyr Gly Ser Lys Asp Arg Pro Trp Ile Trp Asn Ile Pro
290                 295                 300

Tyr Val Lys Ala Pro Asp Thr His Gly Asn Met Trp Val Pro Ser
305                 310                 315

<210> SEQ ID NO 7
<211> LENGTH: 433
<212> TYPE: PRT
<213> ORGANISM: Drosophila melanogaster
<220> FEATURE:
<221> NAME/KEY: misc_feature
<222> LOCATION: (142)..(144)
<223> OTHER INFORMATION: "Xaa" is unknown or other

<400> SEQUENCE: 7

Leu Asn Ser Leu Phe Val Gln Cys Asn Cys Leu Thr Cys Arg Asp Lys
1               5                   10                  15

Pro Leu Leu Leu Tyr Gly Asp Glu Ser Pro Glu Leu Leu Ser Ile
            20                  25                  30

Gly Lys Phe Lys Gln Gln Val Thr Ala Ile Arg Val Lys Met Pro Thr
            35                  40                  45

Pro Phe Ala Thr Ser His Thr Lys Met Met Phe Leu Gly Tyr Ser Asp
        50                  55                  60

Gly Ser Met Arg Val Val Ile Ser Thr Ala Asn Leu Tyr Glu Asp Asp
65                  70                  75                  80

Trp His Asn Arg Thr Gln Gly Leu Trp Ile Ser Pro Lys Leu Pro Ala
                85                  90                  95

Leu Pro Val Asp Ala Asp Thr Gly Ala Gly Glu Ser Leu Thr Gly Phe
            100                 105                 110

Lys Gln Asp Leu Met Leu Tyr Leu Val Glu Tyr Lys Ile Ser Gln Leu
            115                 120                 125
```

```
Gln Pro Trp Ile Ala Arg Ile Arg Asn Ser Asp Phe Ser Xaa Xaa Xaa
    130                 135                 140

Gly Thr Val Ile Ser Val Pro Ser Ser Arg Thr Gln Pro Lys Tyr Cys
145                 150                 155                 160

Arg Phe Asn Leu Ser Ile Val Ser Leu Arg Ser Val Phe Phe Leu Gly
                165                 170                 175

Ser Val Pro Gly Gly His Arg Glu Gly Ser Val Arg Gly His Pro Trp
            180                 185                 190

Gly His Ala Arg Leu Ala Ser Leu Leu Ala Lys His Ala Ala Pro Ile
        195                 200                 205

Asp Asp Arg Ile Pro Val Val Cys Gln Ser Ser Ile Gly Ser Leu
    210                 215                 220

Gly Ala Asn Val Gln Ala Trp Ile Gln Gln Asp Phe Val Asn Ser Leu
225                 230                 235                 240

Lys Lys Asp Ser Thr Pro Val Gly Lys Leu Arg Gln Met Pro Pro Phe
                245                 250                 255

Lys Met Ile Tyr Pro Ser Tyr Gly Asn Val Ala Gly Ser His Asp Gly
            260                 265                 270

Met Leu Gly Gly Gly Cys Leu Pro Tyr Gly Lys Asn Thr Asn Asp Lys
        275                 280                 285

Gln Pro Trp Leu Lys Asp Tyr Leu Gln Gln Trp Lys Ser Ser Asp Arg
    290                 295                 300

Phe Arg Ser Arg Ala Met Pro His Ile Lys Ser Tyr Thr Arg Phe Asn
305                 310                 315                 320

Leu Glu Asp Gln Ser Val Tyr Trp Phe Val Leu Thr Ser Ala Asn Leu
                325                 330                 335

Ser Lys Ala Ala Trp Gly Cys Phe Asn Lys Asn Ser Asn Ile Gln Pro
            340                 345                 350

Cys Leu Arg Ile Ala Asn Tyr Glu Ala Gly Val Leu Phe Leu Pro Arg
        355                 360                 365

Phe Val Val Gly Leu Val Arg Phe Leu Asn Gln Ser Pro Leu Gln Leu
    370                 375                 380

Val Leu Phe Ala Phe Gln Thr Gly Glu Asp Thr Phe Pro Leu Gly Asn
385                 390                 395                 400

Asn Arg Asp Gly Val Pro Ala Phe Pro Leu Pro Tyr Asp Val Pro Leu
                405                 410                 415

Thr Pro Tyr Ala Pro Asp Asp Lys Pro Phe Leu Met Asp Tyr Leu Gln
            420                 425                 430

Gly

<210> SEQ ID NO 8
<211> LENGTH: 451
<212> TYPE: PRT
<213> ORGANISM: Caenorhabditis elegans

<400> SEQUENCE: 8

Met Lys Arg Thr Ile Gln Glu Thr Pro Gly Pro Ser Ser Thr Thr Val
1               5                   10                  15

Pro Pro Lys Lys Leu Asn Ser Gln Arg Asn Gly Ser Asn Leu Glu
            20                  25                  30

Pro Gly Ser Ile Tyr Phe Thr Pro Ile Gly Gly Ile Ser Val Pro Arg
        35                  40                  45

Gln Glu Ser Glu Ser Ser Arg Ser Leu Asp Glu Ile Leu Ala Asp Ile
    50                  55                  60
```

-continued

```
Arg Pro Ile Asn Ser Leu His Phe Ser Phe Met Leu Asp Phe Glu Phe
 65                  70                  75                  80

Leu Ile Gly Ser Tyr Pro Pro Ser Leu Arg Glu Tyr Pro Ile Thr Leu
                 85                  90                  95

Val Val Gly Ala Pro Asp Ala Pro Asp Leu Leu Lys Cys Thr Lys Asn
            100                 105                 110

Gln Lys Leu Val Thr Val Val Gly Ala Ser Leu Pro Ile Pro Phe Gly
        115                 120                 125

Thr His His Thr Lys Met Ser Ile Leu Glu Asp Glu Asp Gly Arg Phe
    130                 135                 140

His Val Ile Val Ser Thr Ala Asn Leu Val Pro Asp Asp Trp Glu Phe
145                 150                 155                 160

Lys Thr Gln Gln Phe Tyr Tyr Asn Phe Gly Val Lys Ile Ala Ser Gly
                165                 170                 175

Thr Val Pro Arg Ser Asp Phe Gln Asp Asp Leu Leu Glu Tyr Leu Ser
            180                 185                 190

Met Tyr Arg Asn Gln Leu Asp Thr Trp Lys Gln Leu Leu Gln Lys Val
        195                 200                 205

Asp Phe Ser Gln Ile Ser Asp Arg Leu Ile Phe Ser Thr Pro Gly Tyr
    210                 215                 220

His Thr Asp Pro Pro Thr Gln Arg Pro Gly His Pro Arg Leu Phe Arg
225                 230                 235                 240

Ile Leu Ser Glu Lys Phe Pro Phe Asp Ala Ser Tyr Glu His Thr Glu
                245                 250                 255

Arg Cys Thr Phe Val Ala Gln Cys Ser Ser Ile Gly Ser Leu Gly Ser
            260                 265                 270

Ala Pro Ile Asn Trp Phe Arg Gly Gln Phe Leu Gln Ser Leu Glu Gly
        275                 280                 285

Ala Asn Pro Ser Pro Lys Gln Lys Pro Ala Lys Met Tyr Leu Val Phe
    290                 295                 300

Pro Ser Val Glu Asp Val Arg Thr Ser Cys Gln Gly Tyr Ala Gly Gly
305                 310                 315                 320

Cys Ser Val Pro Tyr Arg Asn Ser Val His Ala Arg Gln Lys Trp Leu
                325                 330                 335

Gln Gly Asn Met Cys Lys Trp Arg Ser Asn Ala Lys Arg Thr Asn
            340                 345                 350

Ala Val Pro His Cys Lys Thr Tyr Val Lys Tyr Asp Lys Lys Val Ala
        355                 360                 365

Ile Trp Gln Leu Leu Thr Ser Ala Asn Leu Ser Lys Ala Ala Trp Gly
    370                 375                 380

Glu Val Ser Phe Asn Lys Ser Lys Asn Val Glu Gln Leu Met Ile Arg
385                 390                 395                 400

Ser Trp Glu Met Gly Val Leu Ile Thr Asp Pro Ser Arg Phe Asn Ile
                405                 410                 415

Pro Phe Asp Tyr Pro Leu Val Pro Tyr Ser Ala Thr Asp Glu Pro Phe
            420                 425                 430

Val Thr Asp Lys Lys His Glu Lys Pro Asp Ile Leu Gly Cys Ile Trp
        435                 440                 445

Thr Pro Pro
    450

<210> SEQ ID NO 9
<211> LENGTH: 536
```

<212> TYPE: PRT
<213> ORGANISM: Schizosaccharomyces pombe

<400> SEQUENCE: 9

```
Met Ser Thr Leu Glu Pro Glu Lys Arg Arg Gln His Glu Asp Lys Ser
 1               5                  10                  15

Asn Glu Ile Ile Asp Ser Pro Ile Phe Leu Asn Lys Ile Ser Ala Leu
             20                  25                  30

Pro Glu Ser Glu Asn Val His Cys Leu Leu Leu Lys Gln Leu Ile Gly
         35                  40                  45

Ser Pro Gln Leu Lys Gln Thr Trp Gln Phe Asn Phe Cys Val Asp Leu
 50                  55                  60

Asn Phe Leu Leu Glu Asn Met His Ala Ser Val Phe Pro Thr Val Asp
 65                  70                  75                  80

Val Arg Ile Thr His Gly Tyr Asp Ser Lys Ser Asp Ser Leu Ala Arg
                 85                  90                  95

Leu Thr Ala Gln Met Asn His Cys Pro Val Asn Val Lys Leu Tyr Ser
            100                 105                 110

Val Tyr Val Pro Met Trp Gly Thr His His Ser Lys Ile Met Val Asn
        115                 120                 125

Phe Phe Lys Asp Asp Ser Cys Gln Ile Val Ile His Thr Ala Asn Leu
130                 135                 140

Val Glu Pro Asp Trp Ile Gly Met Ser Gln Ala Ile Phe Lys Thr Pro
145                 150                 155                 160

Leu Leu Tyr Pro Lys Ala Asn Asp Ser Leu Ser Thr Ser Ser Val Pro
                165                 170                 175

Glu Tyr Gly Asn Pro Ser Lys Ile Arg Lys His Glu Gly Ser Leu Asp
            180                 185                 190

Ile Lys Asp Asp Arg Asn Cys Asp Ile Ile Asp Val Asp Ser Ala Phe
        195                 200                 205

Glu Asn Phe Lys His Lys Ser Asp Thr Arg Ser Ser Asp Asp Leu Gly
    210                 215                 220

Val Ile Gly Arg Gln Phe Gln Gln Asp Phe Leu Ala Tyr Leu Lys Asn
225                 230                 235                 240

Tyr Arg His Thr Tyr Glu Leu Ile Glu Lys Leu Lys Met Tyr Asp Phe
                245                 250                 255

Ser Ala Ile Arg Ala Ile Phe Ile Gly Ser Val Pro Gly Lys Phe Glu
            260                 265                 270

Gly Glu Glu Ser Ser Trp Gly Leu Gly Lys Leu Lys Lys Ile Leu
        275                 280                 285

Lys Met Leu Glu Lys Asp Ser Lys Lys Asp Glu Lys Thr Lys Phe Glu
290                 295                 300

Glu Ser Asp Ile Cys Ile Ser Gln Cys Ser Ser Met Gly Ser Phe Gly
305                 310                 315                 320

Pro Lys Gln Glu Tyr Ile Ala Glu Leu Thr Asp Gly Phe Gly Cys Gln
                325                 330                 335

Arg Gly Asn Trp Lys Phe Leu Phe Pro Thr Val Lys Glu Val Gln Gln
            340                 345                 350

Ser Met Leu Gly Trp Gln Ser Gly Ser Ser Ile His Phe Asn Ile Leu
        355                 360                 365

Gly Lys Thr Ala Ala Ser Gln Val Glu Thr Leu Lys Lys Gly Lys Asn
    370                 375                 380

Leu Cys Lys Trp Val Ala Met Lys Ala Gly Arg Gln Arg Val Ala Pro
385                 390                 395                 400
```

-continued

```
His Ile Lys Thr Tyr Met Arg Phe Ser Asn Asp Gly Glu Leu Leu Arg
            405                 410                 415

Trp Val Leu Val Thr Ser Ala Asn Leu Ser Lys Pro Ala Trp Gly Thr
            420                 425                 430

Leu Glu Gly His Lys Ala Lys Ser Arg Ser Thr Arg Gly Leu Arg Ile
            435                 440                 445

Arg Ser Tyr Glu Ala Gly Val Leu Leu Tyr Pro Lys Leu Phe Glu Glu
    450                 455                 460

Ser Gln Arg Ala Pro Cys Ile Met Thr Pro Thr Tyr Lys Thr Asn Thr
465                 470                 475                 480

Pro Asn Leu Asp Glu Lys Arg Arg Glu Phe Tyr Gly Lys Arg Val Ile
            485                 490                 495

Gly Val Arg Met Cys Trp Asp Phe Pro Val Glu Tyr Glu Asp Lys
                500                 505                 510

Asp Glu Ile Trp Ser Pro Val Ile Asn Arg Thr Asp Lys Asp Trp Leu
            515                 520                 525

Gly Tyr Val Trp Pro Pro Asn Trp
    530                 535

<210> SEQ ID NO 10
<211> LENGTH: 2
<212> TYPE: PRT
<213> ORGANISM: Homo sapiens
<220> FEATURE:
<221> NAME/KEY: misc_feature
<223> OTHER INFORMATION: Amino acids 622-623 of the deduced amino acid
      sequence of a human cDNA encoding TDP1

<400> SEQUENCE: 10

Glu Ser
1

<210> SEQ ID NO 11
<211> LENGTH: 62
<212> TYPE: PRT
<213> ORGANISM: Homo sapiens
<220> FEATURE:
<221> NAME/KEY: misc_feature
<223> OTHER INFORMATION: Amino acids 625-686 of the deduced amino acid
      sequence of a human cDNA encoding TDP1

<400> SEQUENCE: 11

Gly Thr Val Lys Phe Lys Cys Lys Thr Leu Ser His Lys His Gly Ile
1               5                   10                  15

Ser Ser Leu Tyr Trp Met Ser Thr Ser Leu Lys Val Leu Phe Ala Pro
            20                  25                  30

Leu Gln Asn Leu Ser Lys Gly His Ser Tyr Glu Trp Met Leu Val Ile
        35                  40                  45

Leu Leu Met Asp Ile Asn Ile Pro Asn Lys Val Leu Val Ser
    50                  55                  60

<210> SEQ ID NO 12
<211> LENGTH: 9
<212> TYPE: PRT
<213> ORGANISM: Homo sapiens
<220> FEATURE:
<221> NAME/KEY: misc_feature
<223> OTHER INFORMATION: Amino acides 688-696 of the deduced amino acid
      sequence of a human cDNA encoding TDP1

<400> SEQUENCE: 12
```

```
Lys Lys Lys Lys Lys Lys Lys Lys
1               5

<210> SEQ ID NO 13
<211> LENGTH: 696
<212> TYPE: PRT
<213> ORGANISM: Homo sapiens
<220> FEATURE:
<221> NAME/KEY: misc_feature
<222> LOCATION: (621)..(621)
<223> OTHER INFORMATION: Xaa can be any naturally occurring amino acid
<220> FEATURE:
<221> NAME/KEY: misc_feature
<222> LOCATION: (624)..(624)
<223> OTHER INFORMATION: Xaa can be any naturally occurring amino acid
<220> FEATURE:
<221> NAME/KEY: misc_feature
<222> LOCATION: (687)..(687)
<223> OTHER INFORMATION: Xaa can be any naturally occurring amino acid

<400> SEQUENCE: 13

Glu Ala Ser Val Gly Ser Val Arg Leu Arg Ser Ile Met Ser Gln Glu
1               5                   10                  15

Gly Asp Tyr Gly Arg Trp Thr Ile Ser Ser Asp Glu Ser Glu Glu
            20                  25                  30

Glu Lys Pro Lys Pro Asp Lys Pro Ser Thr Ser Ser Leu Leu Cys Ala
        35                  40                  45

Arg Gln Gly Ala Ala Asn Glu Pro Arg Tyr Thr Cys Ser Glu Ala Gln
    50                  55                  60

Lys Ala Ala His Lys Arg Lys Ile Ser Pro Val Lys Phe Ser Asn Thr
65                  70                  75                  80

Asp Ser Val Leu Pro Pro Lys Arg Gln Lys Ser Gly Ser Gln Glu Asp
                85                  90                  95

Leu Gly Trp Cys Leu Ser Ser Asp Asp Glu Leu Gln Pro Glu Met
            100                 105                 110

Pro Gln Lys Gln Ala Glu Lys Val Ile Lys Lys Glu Lys Asp Ile
        115                 120                 125

Ser Ala Pro Asn Asp Gly Thr Ala Gln Arg Thr Glu Asn His Gly Ala
130                 135                 140

Pro Ala Cys His Arg Leu Lys Glu Glu Glu Asp Glu Tyr Glu Thr Ser
145                 150                 155                 160

Gly Glu Gly Gln Asp Ile Trp Asp Met Leu Asp Lys Gly Asn Pro Phe
                165                 170                 175

Gln Phe Tyr Leu Thr Arg Val Ser Gly Val Lys Pro Lys Tyr Asn Ser
            180                 185                 190

Gly Ala Leu His Ile Lys Asp Ile Leu Ser Pro Leu Phe Gly Thr Leu
        195                 200                 205

Val Ser Ser Ala Gln Phe Asn Tyr Cys Phe Asp Val Asp Trp Leu Val
210                 215                 220

Lys Gln Tyr Pro Pro Glu Phe Arg Lys Lys Pro Ile Leu Leu Val His
225                 230                 235                 240

Gly Asp Lys Arg Glu Ala Lys Ala His Leu His Ala Gln Ala Lys Pro
                245                 250                 255

Tyr Glu Asn Ile Ser Leu Cys Gln Ala Lys Leu Asp Ile Ala Phe Gly
            260                 265                 270

Thr His His Thr Lys Met Met Leu Leu Tyr Glu Glu Gly Leu Arg
        275                 280                 285

Val Val Ile His Thr Ser Asn Leu Ile His Ala Asp Trp His Gln Lys
290                 295                 300
```

-continued

```
Thr Gln Gly Ile Trp Leu Ser Pro Leu Tyr Pro Arg Ile Ala Asp Gly
305                 310                 315                 320

Thr His Lys Ser Gly Glu Ser Pro Thr His Phe Lys Ala Asp Leu Ile
            325                 330                 335

Ser Tyr Leu Met Ala Tyr Asn Ala Pro Ser Leu Lys Glu Trp Ile Asp
                340                 345                 350

Val Ile His Lys His Asp Leu Ser Glu Thr Asn Val Tyr Leu Ile Gly
            355                 360                 365

Ser Thr Pro Gly Arg Phe Gln Gly Ser Gln Lys Asp Asn Trp Gly His
    370                 375                 380

Phe Arg Leu Lys Lys Leu Leu Lys Asp His Ala Ser Ser Met Pro Asn
385                 390                 395                 400

Ala Glu Ser Trp Pro Val Val Gly Gln Phe Ser Ser Val Gly Ser Leu
                405                 410                 415

Gly Ala Asp Glu Ser Lys Trp Leu Cys Ser Glu Phe Lys Glu Ser Met
                420                 425                 430

Leu Thr Leu Gly Lys Glu Ser Lys Thr Pro Gly Lys Ser Ser Val Pro
        435                 440                 445

Leu Tyr Leu Ile Tyr Pro Ser Val Glu Asn Val Arg Thr Ser Leu Glu
    450                 455                 460

Gly Tyr Pro Ala Gly Gly Ser Leu Pro Tyr Ser Ile Gln Thr Ala Glu
465                 470                 475                 480

Lys Gln Asn Trp Leu His Ser Tyr Phe His Lys Trp Ser Ala Glu Thr
                485                 490                 495

Ser Gly Arg Ser Asn Ala Met Pro His Ile Lys Thr Tyr Met Arg Pro
            500                 505                 510

Ser Pro Asp Phe Ser Lys Ile Ala Trp Phe Arg Val Thr Ser Ala Asn
            515                 520                 525

Leu Ser Lys Ala Ala Trp Gly Ala Leu Glu Lys Asn Gly Thr Gln Leu
    530                 535                 540

Met Ile Arg Ser Tyr Glu Leu Gly Val Leu Phe Leu Pro Ser Ala Phe
545                 550                 555                 560

Gly Leu Asp Ser Phe Lys Val Lys Gln Lys Phe Phe Ala Gly Ser Gln
                565                 570                 575

Glu Pro Met Ala Thr Phe Pro Val Pro Tyr Asp Leu Pro Pro Glu Leu
            580                 585                 590

Tyr Gly Ser Lys Asp Arg Pro Trp Ile Trp Asn Ile Pro Tyr Val Lys
    595                 600                 605

Ala Pro Asp Thr His Gly Asn Met Trp Val Pro Ser Xaa Glu Ser Xaa
610                 615                 620

Gly Thr Val Lys Phe Lys Cys Lys Thr Leu Ser His Lys His Gly Ile
625                 630                 635                 640

Ser Ser Leu Tyr Trp Met Ser Thr Ser Leu Lys Val Leu Phe Ala Pro
                645                 650                 655

Leu Gln Asn Leu Ser Lys Gly His Ser Tyr Glu Trp Met Leu Val Ile
            660                 665                 670

Leu Leu Met Asp Ile Asn Ile Pro Asn Lys Val Leu Val Ser Xaa Lys
            675                 680                 685

Lys Lys Lys Lys Lys Lys Lys
690                 695
```